(12) United States Patent
Israeli et al.

(10) Patent No.: US 7,070,782 B1
(45) Date of Patent: Jul. 4, 2006

(54) PROSTATE-SPECIFIC MEMBRANE ANTIGEN

(75) Inventors: Ron S. Israeli, Forest Hills, NY (US); Warren D. W. Heston, New York, NY (US); William R. Fair, New York, NY (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 0 days.

(21) Appl. No.: 08/481,916

(22) Filed: Jun. 7, 1995

Related U.S. Application Data

(63) Continuation of application No. 08/325,553, filed on Oct. 18, 1994, now Pat. No. 5,538,866, which is a continuation of application No. 07/973,337, filed on Nov. 5, 1992, now abandoned.

(51) Int. Cl.
*A61K 39/00* (2006.01)
*C07K 7/00* (2006.01)
*C07K 14/47* (2006.01)

(52) U.S. Cl. .................. 424/185.1; 530/300; 530/326; 530/329; 530/350

(58) Field of Classification Search .............. 424/185.1; 530/300, 326, 329, 350; 435/69.7
See application file for complete search history.

(56) References Cited

U.S. PATENT DOCUMENTS

| | | | |
|---|---|---|---|
| 4,554,101 A | | 11/1985 | Hopp |
| 4,569,794 A | * | 2/1986 | Smith et al. |
| 5,153,118 A | | 10/1992 | Wright, Jr. et al. |
| 5,162,504 A | | 11/1992 | Horoszewicz |
| 5,538,866 A | | 7/1996 | Israeli et al. |
| 5,672,592 A | | 9/1997 | Jackson et al. |
| 5,773,292 A | | 6/1998 | Bander |
| 5,795,877 A | | 8/1998 | Jackson et al. |
| 5,804,602 A | | 9/1998 | Slusher et al. |
| 5,852,167 A | | 12/1998 | Kay et al. |
| 5,863,536 A | | 1/1999 | Jackson et al. |
| 5,880,112 A | | 3/1999 | Jackson et al. |
| 5,902,817 A | | 5/1999 | Jackson et al. |
| 5,935,818 A | | 8/1999 | Israeli et al. |
| 5,939,258 A | | 8/1999 | Croce et al. |
| 5,962,521 A | | 10/1999 | Jackson et al. |
| 5,968,915 A | | 10/1999 | Jackson et al. |
| 5,981,209 A | | 11/1999 | Slusher et al. |
| 6,011,021 A | | 1/2000 | Slusher et al. |
| 6,017,903 A | | 1/2000 | Slusher et al. |
| 6,025,344 A | | 2/2000 | Jackson et al. |
| 6,025,345 A | | 2/2000 | Jackson et al. |
| 6,046,180 A | | 4/2000 | Jackson et al. |
| 6,054,444 A | | 4/2000 | Jackson et al. |
| 6,107,090 A | | 8/2000 | Bander |
| 6,121,252 A | | 9/2000 | Jackson et al. |
| 6,136,311 A | | 10/2000 | Bander |
| 6,150,508 A | | 11/2000 | Murphy et al. |
| 6,271,245 B1 | | 8/2001 | Jackson et al. |
| 6,288,046 B1 | | 9/2001 | Jackson et al. |
| 6,348,464 B1 | | 2/2002 | Jackson et al. |
| 6,372,726 B1 | | 4/2002 | Slusher et al. |
| 6,384,022 B1 | | 5/2002 | Jackson et al. |
| 6,395,718 B1 | | 5/2002 | Slusher et al. |
| 6,413,948 B1 | | 7/2002 | Slusher et al. |
| 6,452,044 B1 | | 9/2002 | Jackson et al. |
| 6,458,775 B1 | | 10/2002 | Jackson et al. |
| 6,479,471 B1 | | 11/2002 | Jackson et al. |
| 6,569,432 B1 | | 5/2003 | Israeli et al. |
| 6,586,623 B1 | | 7/2003 | Tsukamoto et al. |
| 6,649,163 B1 | | 11/2003 | Bander |
| 2001/0044459 A1 | | 11/2001 | Jackson et al. |
| 2002/0013295 A1 | | 1/2002 | Slusher et al. |
| 2002/0015704 A1 | | 2/2002 | Bander |
| 2002/0019430 A1 | | 2/2002 | Jackson et al. |
| 2002/0151503 A1 | | 10/2002 | Slusher et al. |
| 2003/0003101 A1 | | 1/2003 | Bander |
| 2003/0007974 A1 | | 1/2003 | Nanus et al. |
| 2003/0017965 A1 | | 1/2003 | Slusher et al. |
| 2003/0031673 A1 | | 2/2003 | Bander |
| 2003/0064912 A1 | | 4/2003 | Slusher et al. |
| 2003/0083374 A1 | | 5/2003 | Jackson et al. |
| 2003/0105088 A1 | | 6/2003 | Tsukamoto et al. |
| 2003/0216468 A1 | | 11/2003 | Tsukamoto et al. |
| 2004/0001846 A1 | | 1/2004 | Israeli et al. |
| 2004/0024188 A1 | | 2/2004 | Murphy et al. |

FOREIGN PATENT DOCUMENTS

| | | |
|---|---|---|
| EP | 0173951 | 12/1986 |
| WO | WO9409820 | 5/1994 |
| WO | 599626272 | 8/1996 |
| WO | WO9735616 | 10/1997 |
| WO | WO9947554 | 9/1999 |
| WO | 4402096460 | 12/2002 |
| WO | 4502098897 | 12/2002 |

OTHER PUBLICATIONS

Feng et al. *Proc. Amer. Assoc. Cancer Research* 32:239 1991.*
Garcia et al. *J. Bacteriology*, vol. 173, pp. 2093–2098, 1991.*
Bell et al. *Nucleic Acids Research*, vol. 14, pp. 5561–5562, 1986.*
Hartnett et al., *J. Bacteriology*, vol. 172, pp. 956–966, 1990.*
Abdel–Nabi, H. et al. (1992) "Monoclonal Antibodies and Radioimmunoconjugates in the Diagnosis and Treatment of Prostate Cancer", *Seminars in Urology* 127: 45–54.
Axelrod, H.R., et al. (1968) "Preclinical results and human immunohistochemical studies with $^{90}$Y–CYT–356. A new prostate cancer therapeutic agent". Abstract 596. AUA 87th Annucal Meeting, May. 10–14, 1992. Washington, D.C. (1968).

(Continued)

*Primary Examiner*—Gary Kunz
*Assistant Examiner*—Stephen Gucker
(74) *Attorney, Agent, or Firm*—John P. White; Cooper & Dunham LLP

(57) ABSTRACT

The invention provides a purified prostate-specific membrane antigen.

10 Claims, 24 Drawing Sheets

OTHER PUBLICATIONS

Carter, B.H. and Coffey, D.S. (1990) "The Prostate: An Increasing Medical Problem" *The Prostate* 16:39–48.

Feng, Q., et al. (1991) "Purification and Biochemical Characetization of the 7E11–C5 Prostate Carcinoma–Associated Antigen", *Proceedings of the American Association for Cancer Research* 32:239.

Chang, Chawnshang, et al. (1988) "Structural Analysis of Complementary DNA and Amino Acid Sequences of Human and Rat Androgen Receptors", Proc. Natl Acad. Sci USA 85:7211–7215.

Culver, K.W. et al. (1992) "In Vivo Gene Transfer with Retoviral Vector–Producer Cells for Treatment of Experimental Brain Tumors", Science 256:1150–1552.

Decensi A, et al (1991) "Phase II Study of the Pure Non-–Steroidal Antiandrogen Nilutamde in Prostatic Cancer", Eur J Cancer 27:1100–1104.

Faber, P.W. et al. (1991) "Characterization of the Human Androgen Transcription Unit" The Journal of Biological Chemistry 266:10743–10749.

Fey, Martin F. et al. (1991) "The Polymerase Chain Reaction: A New Tool for the Detection of Minimal Residual Disease in Haematological Malignancies" Eur J Cancer 27:89–94.

Henttu, Pirkko and Pirkki (1989) "cDNA Coding for the Entire Human Prostate Specific Antigen Shows High Homologies to the Human Tissue Kallikrein Genes" *Biochemical and Biophysical Research Communications* 160:903–910.

Horoszewicz, Julius S. et al. (1987) "Monoclonal Antibodies to a New Antigen Marker in Epithelial Prostatic Cells and Serum of Prostatic Cancer Patients" *AntiCancer Research* 7:927–936.

Huber, Brian E. et al. (1991) "Retroviral–mediated Gene Therapy for the Treatment of Hepatocellular Carcinoma: An Innovative Approach for Cancer Therapy" *Proc. Natl. Acad. Sci. USA* 88:8039–8043.

Israeli, Ron S., et al. (1994) "Expression of the Prostate Specific Membrane Antigen" *Cancer Research* 54:1807–1811.

Israeli, Ron S. et al. (1994) "Sensitive Nested Reverse Transcription Polymerase Chain Reaction Detection of Circulating Prostatic Tumor Cells: Comparison of Prostate–specific Membrane Antigen and Prostate–specific Antigen–based Assays" Cancer Research 54:6306–6310.

Keer, Harold N., et al. (1990) "Elevated Transferrin Receptor Content in Human Prostate Cancer Cell Lines Assessed In Vitro and In Vivo" *Journal of Urology* 143:381385.

Lopes, A. Dwight., et al (1993) "Immonohistochemical and Pharmacokinetic Characterization of the Site–specific Immunocnjugate CYT–356 Derived from Antiprostate Monoclonal Antibody" *Cancer Research* 50: 6423–6429.

Lubahn, Dennis B., et al. (1989) "Sequence of the Intron/exon junctions of the Coding Region of the Human Adrogen Receptor Gene and Identification of a Point Mutation in a family with Complete Androgen Insensitivity" *Proc. Natl. Acad. Sci. USA* 86:9534–9538.

Lundwall, Ake and Lilja, Hans., (1987) "Molecular Cloning of Human Prostate Specific Antigen cDNA" 214, No. 2:317–322.

Mukhopadhyay, Tapas., et al. (1991) "Specific Inhibition of K–ras Expression and Tumorigenicity of Lung Cancer Cells by Antisense RNA[1]" *Cancer Research* 51:1744–1748.

Riegman, P.H.J., et al. (1989) "The Prostate–Specific Antigen Gene and the Human Glandular Kallikrein–1 Gene are Tandemly Located on Chromosone 19" vol. 247:123–126.

Solin, Timo., (1990) "Gene Expression and Prostate Specificity of Human Prostatic Acid Phosphatase (PAP): Evaluation By RNA Blot Analuses" *Biochemica et Biophysica Acta* 1048:72–77.

Troyer, Abstract C38(1994).

Su, S.L., et al. (1994) "Sensitive Detection of Prostatic Hematogenous Micrometastases Using Prostate Specific Antigen (PSA) and Prostate Specific Membrane Antigen (PSM) Derived parimeters in the Polymerase Chain Reaction" *Proceedings of the American Association for Cancer Research* 35:271.

Vihko, Pirkko., et al (1988) "Molecular Cloning and Sequence Analysis of cDNA Encoding Human Prostatic Acid Phosphatase" 236:275–281.

Vile, Richard G. and Ian R. Hart., (1993) "In Vitro and In Vivo Targeting of Gene Expression to Melanoma Cells" *Cancer Research* 53:962–967.

Israeli, Ron S., et al. (1993) "Molecular Cloning of a Complementary DNA Encoding a Prostate–specific Membrane Antigen" *Cancer Research* 53:227–230.

Waibel, R., et al. (1990) "Therapy of Small Cell Lung Cancer Xenografts in a Nude Mouse model: Evaluation of Radioimmunotherapy and Immonotoxin Therapyogy" 34:54.

Watt, Kenneth W.K., et al (1986) "Human Prostate–Specific Antigen: Structural and Functional Similarity With Serine Proteases" *Proc. Natl. Acad. Sci. USA* 83:3166–3170.

Wright, Jr., et al., (1990) "Characterization of a New Prostate Carcinoma–Associated Marker" *Antibody Immunoconjugates and Radiopharmaceuticals* 3:89.

Young, Richard A. and Davis, Ronald W., (1983) "Efficient Isolation of Genes by Using Antibody Probes" *Proc. Natl. Acad. Sci. USA* 80:1194–1198.

Israeli, R.S. et al. (1994) "Sensitive Detection of Prostatic Hematogenous Micro–Metastases Using Prostate Specific Antigen (PSA) And Prostate Specific Membrane Antigen (PSM) Derived Primers in the Polymerase Chain Reaction (PCR)" J Urol 151:373A.

Israeli, R.S. et al.; (1994) "Localization of the Prostate Specific Membrane Antigen (PSM) to the Putative Mestatsis–Suppressor Region on Human Chromosome 11" J Urol 151:492A.

Corr, J.G. et al., (1994) "Prostate Specific Membrane Antigen (PSM) Expression in Orthotopically Implanted Human Procstate Cancer Cells in Nude Mice Slows Tumor Growth and Netastatic Potential" J Urol 151:492A.

Israeli, R.S. et al., (1994) "Localization of the Prostate Specific Membrane Antigen (PSM) to the Putative Metastasis–Suppressor Region on Human Chromosome 11" Proceedings of the American Association for Cancer Research 35:271.

Israeli, R.S. et al., (1993) "Characterization of the Prostate–Specific Membrane Antigen (PSM)" Cancer Research 34:255.

Israeli, R.S. et al., (1993) "Molecular Cloning and Characterization of a Prostate–Specific Membrane Antigen" J Urol 149:471A.

Israeli, R.S. et al., (1992) "Purification and Molecular Cloning of a New Prostate–Specific Antigen" Cancer Research 33:356.

Translation of the Abstract of EP 0 173 951, i.e. Reference 13 (Exhibit 5).

Tortora, G.J., et al., (1989) *Microbiology, An Indroduction*, Benjamin/Cummings Publishing Co., 423–426, 471 (Exhibit 6).

Stites, D.P., (1991) *Basic and Clinical Immunology*, Appleton & Lange, 229–251 (Exhibit 7).

Rose, N.R., et al., (1986) *Manual of Clinical Laboratory Immunology*, American Society for Microbiology, 89–109 (Exhibit 8).

Paul, W.E. (1989) *Fundamental Immunology*, Raven Press, 628–629, 647–651 (Exhibit 9).

Gately, M.K. et al., (1992) "Regulation of Human Cytololytic Lymphocyte Responses by Interleukin–12", *Cellular Immunology* 143:381–385 (Exhibit 10).

Rossi, M.C. & Zetter, B.R., (1992) "Selective Stimulation of Prostatic Carcinoma Cell Proliferation by Transferrin", *PNAS* 89:6197–6201 (Exhibit 11).

Sambrook, J. et al., (1989) *Molecular Cloning, A Laboratory Manual*, Cold Spring Harbor Laboratory Press, 16.1–16.81 (Exhibit 12).

Schneider, C. et al., (1984) "Primary Structure of Human Transferrin Receptor Deduced from the mRNA sequence", *Nature* 311:675–678 (Exhibit 13).

Su, S.L., et al. (1995) Cancer Research, 55, 7:1441–1443 (Exhibit 1).

Sharief, F.S., Lee, H., Leuderman, M.M., Lundwall, A., Deaven, L.L., Lee, C.L. and Li, S.S. (1989) Human prostatic acid phosphatase: cDNA cloning, gene mapping and protein sequence homology with lysosomal acid phosphatase. Biochem. Biophys. Res. Commun. 160: 79–86.

U.S. patent application Ser No. 08/403,803, Israeli et al., filed Mar. 17, 1995.

U.S. patent application Ser No. 08/466,381, Israeli et al., filed Jun. 6, 1995.

U.S. patent application Ser No. 08/470,735, Israeli et al., filed Jun. 6, 1995.

U.S. patent application Ser No. 09/724,026, Israeli et al., filed Nov. 28, 2000.

U.S. patent application Ser No. 09/990,595, Israeli et al., filed Nov. 21, 2001.

U.S. patent application Ser No. 10/012,169, Israeli et al., filed Oct. 24, 2001.

U.S. patent application Ser No. 10/614,625, Israeli et al., filed Jul. 2, 2003.

Preliminary Amendment re Exhibit 55, Israeli et al., filed Jul. 2, 2003.

U.S. patent application Ser No. 08/894,583, Israeli et al., filed Feb. 23, 1998.

U.S. patent application Ser No. 10/751,346, Israeli et al., filed Jan. 2, 2004.

U.S. patent application Ser No. 09/357,704, Bander, filed Jul. 20, 1999.

U.S. patent application Ser No. 09/357,707, Bander, filed Jul. 20, 1999.

U.S. patent application Ser No. 09/357,708, Bander, filed Jul. 20, 1999.

U.S. patent application Ser No. 09/357,709, Bander, filed Jul. 20, 1999.

U.S. patent application Ser No. 09/357,710, Bander, filed Jul. 20, 1999.

U.S. patent application Ser No. 09/929,546, Bander, filed Aug. 13, 2001.

U.S. patent application Ser No. 09/929,665, Bander, filed Aug. 13, 2001.

U.S. patent application Ser No. 09/561,462, Murphy et al., filed Apr. 28, 2000.

U.S. patent application Ser No. 09/561,502, Murphy et al., filed Apr. 28, 2000.

U.S. patent application Ser No. 09/724,630, Murphy et al., filed Nov. 28, 2000.

* cited by examiner

Western Analysis of LNCaP Membrane Proteins

1 - anti- EGFr PoAB RK-2
2 - Cyt-356 MoAB/RAM
3 - RAM

MSKCC Urologic Oncology Laboratory

FIGURE 12
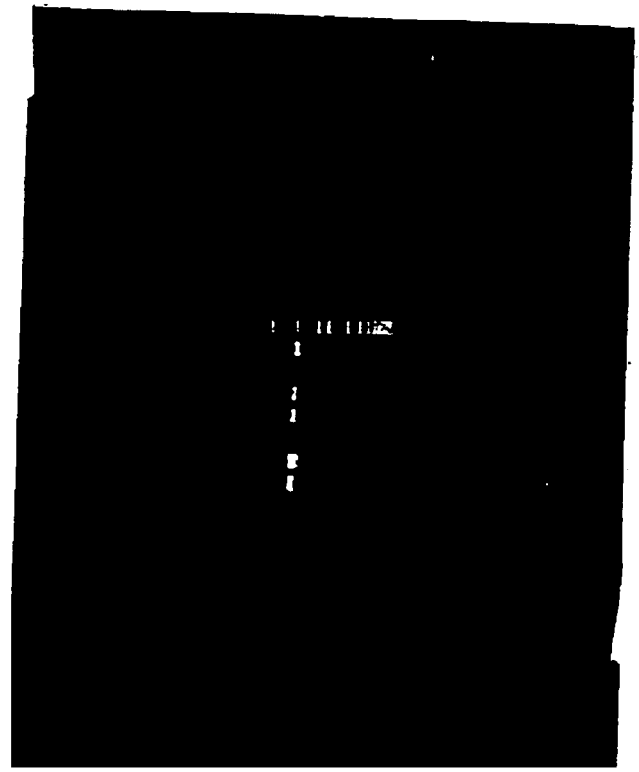

Program CHARGPRO

Residues and pK values taken in account in the computation.

N-ter (+) Met, pK: 9.21
C-ter (-) Ala, pK: 2.34

Arg (+)  35, pK: 12.48
Lys (+)  45, pK: 10.79
His (+)  16, pK: 6

Asp (-)  36, pK: 3.65
Glu (-)  48, pK: 4.25
Cys (-)   5, pK: 8.35
Tyr (-)  39, pK: 10.13

Isoelectric point: 6.5

Curve of the charge of protein PRSANTIGEN as a function of the pH (from 0 to 14)
Calculated on the complete sequence, 758 residues.

FIGURE 14 one on sequence PMSANTIGEN.
otal number of residues is: 750.
nalysis done on the complete sequence.

```
n Helical   (H) conformation [DC =  -75 CNAT ] :  264 AA => 35.2%
n Extended  (E) conformation [DC =  -88 CNAT ] :  309 AA => 41.2%
n   Turn    (T) conformation [DC =    0 CNAT ] :   76 AA => 10.1%
n   Coil    (C) conformation [DC =    0 CNAT ] :  101 AA => 13.4%
``` equence shown with conformation codes.

onsecutive stretch of 5 or more residues in a given conformation are
verlined.

Semi-graphical output.
==========================

Symbols used in the semi-graphical representation:

Helical conformation: X         Extended conformation: -
  Turn conformation: >            Coil conformation: *

```
             10         20         30         40         50
              |          |          |          |          |
     MWNLLHETDSAVATARRPRWLCAGALVLAGGFFLLGFLFGWFIKSSNEAT

XXXXXXXXXXXXXX--->>-----------------XXXXXX******>X
     XXXXXXXXXXXXXX--->>-----------------XXXXXX******>X 60         70         80         90        100
              |          |          |          |          |
     NITPKHNMKAFLDELKAENIKKFLYNFTQIPHLAGTEQNFQLAKQIQSQW

XXXXXXXXXXXXXXXXXXXXXXX--->>-----*****XXXXXXXXX-X*--
     XXXXXXXXXXXXXXXXXXXXXXX--->>-----*****XXXXXXXXX-X*--

110        120        130        140        150
              |          |          |          |          |
     KEFGLDSVELAHYDVLLSYPNKTHPNYISIINEDGNEIFNTSLFEPPPPG

->>XXXXXXXXX----->>>---------*>X----->>**>>
     ->>XXXXXXXXX----->>>---------*>X----->>**>>

160        170        180        190        200
              |          |          |          |          |
     YENVSDIVPPFSAFSPQGMPEGDLVYVNYARTEDFFKLERDMKINCSGKI
```

FIGURE 14 (CONT'D)

```
>----------->-**>***----------XXXXXXXXXXXXXXXX>>>--
>----------->-**>***----------XXXXXXXXXXXXXXXX>>>--
        210       220       230       240       250
         |         |         |         |         |
      VIARYGKVFRGNKVKNAQLAGAKGVILYSDPADYFAPGVKSYPDGWNLPG

----------->>XXXXXXXX--------->>----->----->>>>->
----------->>XXXXXXXX--------->>----->----->>>>->
        260       270       280       290       300
         |         |         |         |         |
      GGVQRGNILNLNGAGDPLTPGYPANEYAYRRGIAEAVGLPSIPVHPIGYY

>*---------->>>*------***-----XX---------*----------
>*---------->>>*------***-----XX---------*----------
        310       320       330       340       350
         |         |         |         |         |
      DAQKLLEKMGGSAPPDSSWRGSLKVPYNVGPGFTGNFSTQKVKMHIHSTN

XXXXXXX->>>****>->>->--------------*-*XXXXX---****
XXXXXXX->>>****>->>->--------------*-*XXXXX---****
        360       370       380       390       400
         |         |         |         |         |
      EVTRIYNVIGTLRGAVEPDRYVILGGHRDSWVFGGIDPQSGAAVVHEIVR

--------------------------***>---->>***>**XXX----XX
--------------------------***>---->>***>**XXX----XX
        410       420       430       440       450
         |         |         |         |         |
      SFGTLKKEGWRPRRTILFASWDAEEFGLLGSTEWAEENSRLLQERGVAYI

XXX***>>>***>------*XXXXXXXX***XXXXXXXXXXXX------
XXX***>>>***>------*XXXXXXXX***XXXXXXXXXXXX------
        460       470       480       490       500
         |         |         |         |         |
      NADSSIEGNYTLRVDCTPLMYSLVHNLTKELKSPDEGFEGKSLYESWTKK

----->>------------XXXXXXXXXXXXXXXXXXXXX>>>*
----->>------------XXXXXXXXXXXXXXXXXXXXX>>>*
        510       520       530       540       550
         |         |         |         |         |
      SPSPEFSGMPRISKLGSGNDFEVFFQRLGIASGRARYTKNWETNKFSGYP

****>-----------****---XXXXX>***--->>-*>>->>>>>*--
****>-----------****---XXXXX>***--->>-*>>->>>>>*--
        560       570       580       590       600
         |         |         |         |
```

FIGURE 14 (CONT')

```
LYHSVYETYELVEKFYDPMFKYHLTVAQVRGGMVFELANSIVLPFDCRDY

------XXXXXXXXXXXXXXXXX-X--------XXXX------>XXX
------XXXXXXXXXXXXXXXXX-X--------XXXX------>XXX 610       620       630       640       650
         |         |         |         |         |
AVVLRKYADKIYSISMKHPQEMKTYSVSFDSLFSAVKNFTEIASKFSERL

XXXXXXXXXX-----X**XXXXX-------XXXXXXXXXXXXXXXXXXX
XXXXXXXXXX-----X**XXXXX-------XXXXXXXXXXXXXXXXXXX 660       670       680       690       700
         |         |         |         |         |
QDFDKSNPIVLRMMNDQLMCLERAFIDPLGLPDRPFYRHVIYAPSSHNKY

XX>>>------XXXXXXXXXXXX-->>*>------------>***>
XX>>>------XXXXXXXXXXXX-->>*>------------>***>

710       720       730       740       750
         |         |         |         |         |
AGESFPGIYDALFDIESKVDPSKAWGEVKRQIYVAAFTVQAAAETLSEVA

------>--XXXXXXXX***XXXXXXX--------XXXXXXXXXXXX
------>--XXXXXXXX***XXXXXXX--------XXXXXXXXXXXX
```

FIGURE 15B

```
************************************
* PREDICTION OF ANTIGENIC DETERMINANTS *
************************************

Done on sequence PMSANTIGEN.
Total number of residues is: 750.
Analysis done on the complete sequence.

The method used is that of Hopp and Woods.
The averaging group length is: 6 amino acids.
-> This is the value recommended by the authors <-
_____

The three highest points of hydrophilicity are:

( 1)  Ah= 1.62 : From   63 to   68 : Asp-Glu-Leu-Lys-Ala-Glu
( 2)  Ah= 1.57 : From  132 to  137 : Asn-Glu-Asp-Gly-Asn-Glu
( 3)  Ah= 1.55 : From  482 to  487 : Lys-Ser-Pro-Asp-Glu-Gly Ah stands for: Average hydrophilicity.

Note that, on a group of control proteins, only the highest point was in 100%
of the cases assigned to a known antigenic group. The second and third points
gave a proportion of 33% of incorrect predictions.
```

FIGURE 16

```
The best scores are:                                          initn  init1  opt
CHKTFER   G.gallus mRNA for transferrin receptor               203    120   321
RATTRFR   Rat transferrin receptor mRNA, 3' end.               164    164   311
HUMTFRR   Human transferrin receptor mRNA, complete cd         145    145   266

CHKTFER   G.gallus mRNA for transferrin receptor                203    120   321
  51.9% identity in 717 nt overlap 1020      1030      1040      1050      1060      1070
pmsgen  TGTCCAGCGTGGAAATATCCTAAATCTGAATGGTGCAGGAGACCCTCTCACACCAGGTTA
         :::    :  :::::::::   :::  :::::   :
CHKTFE  TACACTTATCCCATTCGGACATGCCCACCTTGGAACTGGAGACCCTTACACCCCAGGCTT
              990      1000      1010      1020      1030      1040

1080      1090      1100      1110      1120      1130
pmsgen  CCCAGCAAATGAATATGCTTATAGGCGTGGAATTGCAGAGGCTGTTGGTCTTCCAAGTAT
         :::  :       :   :   :    :   ::   ::    :: :: ::       ::
CHKTFE  CCCTTCGTTCAACCACACCCA---GTTTCCACCAGTTGAATCTTCAGGACTACCCCACAT
              1050      1060      1070      1080      1090      1100

1140      1150      1160      1170      1180      1190
pmsgen  TCCTGTTCATCCAATTGGATACTATGATGCACAGAAGCTCCTAGAAAAAAATGGGTGGCTC
         : :::::::  : ::      :  :: :::     : :::  :      :::::::  :::
CHKTFE  TGCTGTTCAGACCATCTCTAGCAGTGCAGCAGCCAGGCTGTTCAGCAAAATGGATGGAGA
              1110      1120      1130      1140      1150      1160

1200      1210      1220      1230      1240      1250
pmsgen  AGCACCACCAGATAGCAGCTGGAGAGGAAGTCTCAAAGTGCCCTACAATGTTGGACCTGG
         ::      : ::  : :::::  :::       ::  :           :::  :: ::  :::
CHKTFE  CACATGCTCTGA-AG--GTTGGAAAGGTGCGATCCA---TTCCTGTAAGGT--GAC--AA
              1170      1180      1190      1200                1210

1260      1270      1280      1290      1300      1310
pmsgen  CTTTACTGGAAACTTTTCTACACAAAAAGTCAAGATGCACATCCACTCTACCAATGAAGT
         :    :  :::  :      : :   :    ::  ::   :  :  :: : :::       :::
CHKTFE  CAAAGCAGGAGA----GCCAGA-TAATGGTGAAACTAGATGTGAACAATTCCATGAAAGA
              1220          1230      1240      1250      1260

1320      1330      1340      1350      1360      1370
pmsgen  GACAAGAATTTACAATGTGATAGGTACTCTCAGAGGAGCAGTGGAACCAGACAGATATGT
         :   :   :::    ::    :   :::  ::    :::    :   ::::::  ::    : :::::
CHKTFE  CAGGAAGATTCTGAACATCTTCGGTGCTATCCAGGGATTTGAAGAACCTGATCGGTATGT
              1270      1280      1290      1300      1310      1320

1380      1390      1400      1410      1420      1430
pmsgen  CATTCTGGGAGGTCACCGGGACTCATGGGTGTTTGGTGGTATTGACCCTCAGAGTGGAGC
         :  :  ::::   ::   :  ::::::  ::::       ::  :    :  :::   :: :::::   :
CHKTFE  TGTGATTGGAGCCCAGAGAGACTCCTGGGGCCCAGGAGTGGCTAAAGCTGGCACTGGAAC
              1330      1340      1350      1360      1370      1380
```

FIGURE 16 (CONT'D)

```
          1440      1450      1460      1470      1480      1490
pmsgen AGCTGTTGTTCATGAAATTGTGAG---GAGCTTTGGAACACTGAAAAAGGAAGGGTGGAG
       ::: : .:    ::: :::    :  :: ::   :  : : :::::::: :: ::  : :
CHKTFE TGCTATATTGTTGGAACTTGCCCGTGTGATCTCAGACATAGTGAAAAACGAGGGCTACAA
          1390      1400      1410      1420      1430      1440

1500      1510      1520      1530      1540      1550
pmsgen ACCTAGAAGAACAATTTTGTTTGCAAGCTGGGATGCAGAAGAATTTGGTCTTCTTGGTTC
       ::: ::  :::   ::   : X::::  :::::::  :::::  :::  : ::   : :::  :
CHKTFE ACCGAGGCGAAGCATCATCTTTGCTAGCTGGAGTGCAGGAGACTACGGAGCTGTGGGTGC
          1450      1460      1470      1480      1490      1500

1560      1570      1580      1590      1600      1610
pmsgen TACTGAGTGGGCAGAGGAGAATTCAAGACTCCTTCAAGAGCGTGGCGTGGCTTATATTAA
       ::::::: :::   :::: :  : :X         :  :: ::  :    :  : :::: :: :.
CHKTFE TACTGAATGGCTGGAGGGGTACTCTGCCATGCTGCATGCCAAAGCTTTCACTTACATCA-
          1510      1520      1530      1540      1550      1560

1620      1630      1640      1650      1660      1670
pmsgen TGC-TGACTCATCTATAGAAGGAAACTA-CACTCTGAGAGTTGATTGTACACCGCTGATG
       :: ::  :  :: ::   :: : : : :    : : :    :: :  :  : :: :: ::
CHKTFE -GCTTGGATGCTCCAGTCCTGGGAGCAAGCCATGTCAAGATTTCTGCCAGCCCCTTGCTG
          1570      1580      1590      1600      1610      1620

1680      1690      1700      1710      1720      1730
pmsgen TACAGCTTGGTACACAACCTAACAAAAGAGCTGAAAAGCCCTGATGAAGGCTTTGAAGGC
       :: :  :: :    :   : :  :: : :::: :  ::: :  : ::  ::  :; ::
CHKTFE TATATGCTGCTGGGGAGTATTATGAAGGGGGTGAAGAATCCAGCAGCAGTCTCAGAGAGC
          1630      1640      1650      1660      1670      1680

1740      1750      1760      1770      1780      1790
pmsgen AAATCTCTTTATGAAAGTTGGACTAAAAAAAGTCCTTCCCCAGAGTTCAGTGGCATGCCC
       :::: ::   : : ::::  : : :
CHKTFE ----CTCTATAACAGACTTGGCCCAGACTGGGTAAAAGCAGTTGTTCCTCTTGGCCTGGA
              1690      1700      1710      1720      1730

RATTRFR    Rat transferrin receptor mRNA, 3' end.          164  164  311
  55.5% identity in 560 nt overlap 1210      1220      1230      1240      1250
pmsgen CCACCAGATAGCAGCTGGAGAGGAAGTCTCAAAGTGCCCTACAATGTTGGACCTGGCTT-
                           :::  ::  :::: :  :   : : :    : : ::
RATTRF TGCAGAAAAGCTATTCAAAAACATGGAAGGAAACTGTCCTCCTAGTTGGAATATAGATTC
         610       620       630       640       650       660

1260      1270      1280      1290      1300      1310
pmsgen -TACTGGAAACTTTTCTACACAAAAAGTCAAGATGCACATC-CACTCT-ACCAATG----
       :  ::  ::  ::         ::   :  :::: :::    : : :::: :  : :::::
RATTRF CTCATGTAAGCTGGAACTTTCACAGAATCAAAATGTGAAGCTCACTGTGAACAATGTACT
         670       680       690       700       710       720
```

FIGURE 16 (CONT'D)

```
             1320      1330      1340      1350      1360      1370
pmsgen --AAGTGACAAGAATTTACAATGTGATAGGTACTCTCAGAGGAGCAGTGGAACCAGACAG
        :::  :::::::: ::   :  ::   : :  :::    : :::::::::: :
RATTRF GAAAGAAACAAGAATACTTAACATCTTTGGCGTTATTAAAGGCTATGAGGAACCAGACCG
          730       740       750       760       770       780

1380      1390      1400      1410      1420      1430
pmsgen ATATGTCATTCTGGGAGGTCACCGGGACTCATGGGTGTTTGGTGGTATTGACCCTCAGAG
        ::  :  :  ::::  ::  :::  : ::::    :::: ::   ::   :::  :
RATTRF CTACATTGTAGTAGGAGCCCAGAGAGACGCTTGGGGCCCTGGT-GTTGCGAAGTCCAGTG
          790       800       810       820       830       840

1440     1450      1460      1470      1480
pmsgen T-GGAGCAGCTGTTGTTCATGAAATTGTGAGGAGCTTTGGAACA-CTGA---AAAAGGAA
        : :::  ::: : ::  :  :::::  :   ::  ::  : :::     ::: ::
RATTRF TGGGAACAGGTCTT-CTGTTGAAACTTGCCCAAGTATTCTCAGATATGATTTCAAAAGAT
          850       860       870       880       890       900

1490      1500      1510      1520      1530      1540
pmsgen GGGTGGAGACCTAGAAGAACAATTTTGTTTGCAAGCTGGGATGCAGAAGAATTTGGTCTT
        ::  :    X::::  ::  ::   :  ::  :::::  ::::::   ::::: ::: ::: :
RATTRF GGATTTAGACCCAGCAGGAGTATTATCTTTGCCAGCTGGACTGCAGGAGACTATGGAGCT
          910       920       930       940       950       960

1550      1560      1570      1580      1590      1600
pmsgen CTTGGTTCTACTGAGTGGGCAGAGGAGAA---TTCAAGACTCCTTCAAGAGCGTGGCGTG
        :::::  : ::::::::::  ::::  : X         :  :: :: :    :    :
RATTRF GTTGGTCCGACTGAGTGGCTGGAGGGGTACCTTTCATCTTTGCATCTAAAG---GCTTTC
          970       980       990       1000      1010      1020

1610      1620      1630      1640      1650      1660
pmsgen GCTTATATTAATGCTGACTCATCTATAGAAGGAAACTA-CACTCTGAGAGTTGATTGTAC
        ::::  ::::::: :::    : :  :       ::  ::::  ::   :  :::   :  :
RATTRF ACTTACATTAAT-CTGGATAAAGTCGTCCTGGGTACTAGCAACTTCAAGGTTTCTGCCAG
          1030      1040      1050      1060      1070      1080

1670      1680      1690      1700      1710      1720
pmsgen ACCGCTGATGTACAGCTTGGTACACAACCTAACAAAAGAGCTGAAAAGC-CCTGATGAAG
        :: ::   : ::   :    :  :   ::  :::    : ::   : :::::   : ::
RATTRF CCCCCTATTATATACACTTATGGGAAGATAATGCAGGA--CGTAAAGCATCCGA-----
          1090      1100      1110      1120      1130

1730      1740      1750      1760      1770
pmsgen GCTTTGAAGGCAAATCTCTTTAT-GAA-----AGTTGGACTAAAAAAAGTCCTTCCCCAG
        ::::  :: ::::   :::  ::: :::       : :::::  ::  ::::  :
RATTRF ---TTGATGGAAAATATCTATATCGAAACAGTAATTGGATTAGCAAAATTGAGGAACTTT
            1140      1150      1160      1170      1180      1190

1780      1790      1800      1810      1820      1830
pmsgen AGTTCAGTGGCATGCCCAGGATAAGCAAATTGGGATCTGGAAATGATTTTGAGGTGTTCT RATTRF CCTTGGACAATGCTGCATTCCCTTTTCTTGCATATTCAGGAATCCCAGCAGTTTCTTTCT
          1200      1210      1220      1230      1240      1250
```

FIGURE 16 (CONT'D)

```
HUMTFRR   Human transferrin receptor mRNA, complete cd  145   145   266
  54.3% identity in 464 nt overlap
                1230      1240      1250      1260      1270
pmsgen  AGGAAGTCTCAAAGTGCCCTACAATGTTGGACCTGGCTTTAC-TGGAAACTTTTCTACAC
          :   :  ::  :::   ::  :        :     :       : :
HUMTFR  TATGGAAGGAGACTGTCCCTCTGACTGGAAAACAGACTCTACATGTAGGATGGTAACCTC
         1140      1150      1160      1170      1180      1190

1280      1290      1300      1310         1320      1330
pmsgen  AAAAAGTCAAGATGCACATC-CACTCT-ACCAATG------AAGTGACAAGAATTTACAA
         :  ::::    :  :::      : ::::: : :  ::::       :::  ::  :: ::::         ::
HUMTFR  AGAAAGCAAGAATGTGAAGCTCACTGTGAGCAATGTGCTGAAAGAGATAAAAATTCTTAA
         1200      1210      1220      1230      1240      1250

1340      1350      1360      1370      1380      1390
pmsgen  TGTGATAGGTACTCTCAGAGGAGCAGTGGAACCAGACAGATATGTCATTCTGGGAGGTCA
          :  : ::       : :  :::         ::   ::::::::       ::::::   :    :  ::        ::
HUMTFR  CATCTTTGGAGTTATTAAAGGCTTTGTAGAACCAGATCACTATGTTGTAGTTGGGGCCCA
         1260      1270      1280      1290      1300      1310

1400      1410      1420      1430      1440      1450
pmsgen  CCGGGACTCATGGGTGTTTGGTGGTATTGACCCTCAGAGT-GGAGCAGCTGTTGTTCATG
           :  ::      ::::::       :::  : :          :  : :  : ::   ::      :::::   :       :
HUMTFR  GAGAGATGCATGGGGCCCTGGAGCTGCAAAATC-CGGTGTAGGCACAGCTCTCCTATTGA
         1320      1330      1340      1350      1360      1370

1460      1470      1480      1490      1500
pmsgen  AAATTG---TGAGGAGCTTTGGAACACTGAAAAAGGAAGGGTGGAGACCTAGAAGAACAA
         ::  :::        ::  :    ::    :   :      :      :::  ::  X:::          ::  ::  ::::       :
HUMTFR  AACTTGCCCAGATGTTCTCAGATATGGTCTTAAAAGATGGGTTTCAGCCCAGCAGAAGCA
         1380      1390      1400      1410      1420      1430

1510      1520      1530      1540      1550      1560
pmsgen  TTTTGTTTGCAAGCTGGGATGCAGAAGAATTTGGTCTTCTTGGTTCTACTGAGTGGGCAG
         ::  :  :::::::  ::  :::       :::  :  :::  :::::           :::::  :  :::::  :::     ::
HUMTFR  TTATCTTTGCCAGTTGGAGTGCTGGAGACTTTGGATCGGTTGGTGCCACTGAATGGCTAG
         1440      1450      1460      1470      1480      1490

1570      1580      1590      1600      1610      1620
pmsgen  A-GGAGAATTCAAGACTCCTTCAAGAGCGTGGCGTGGCTTATATTAATGCTGACTCATCT
           :  :::  :       :      :  :  :::   ::         :       :  :::::::::::X   ::         :  :
HUMTFR  AGGGATACCTTTCGTC-CCTGCATTTAAAGGCTTTCACTTATATTAATCTGGATAAAGCG
         1500      1510      1520      1530      1540      1550

1630      1640      1650      1660      1670      1680
pmsgen  ATAGAAGGAAACTACACTCTGAGAGTTGATTGTACACCGCTGATGTACA-GCTTGGT-AC
          :     ::  :  :     ::   :  :  :::    :    :  ::  :::  ::::  :  ::::    :  :
HUMTFR  GTTCTTGGTACCAGCAACTTCAAGGTTTCTGCCAGCCCACTGTTGTATACGCTTATTGAG
         1560      1570      1580      1590      1600      1610
```

FIGURE 16 (CONT'D)

```
          1690      1700      1710      1720      1730      1740
pmsgen ACAACCTAACAAAAGAGCTGAAAAGCCCTGATGAAGGCTTTGAAGGCAAATCTCTTTATG
       : :::      :::::
HUMTFR AAAACAATGCAAAATGTGAAGCATCCGGTTACTGGGCAATTTCTATATCAGGACAGCAAC
          1620      1630      1640      1650      1660      1670
```

Library scan:  0:57:00  total CPU time:  0:57:40

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 2653 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens
      (F) TISSUE TYPE: Carcinoma (vii) IMMEDIATE SOURCE:

-continued (B) CLONE: Prostate-Specific Membrane Antigen (ix) FEATURE:
 (A) NAME/KEY: CDS
 (B) LOCATION: 262..2511

(xi) SEQUENCE DESCRIPTION: SEQ ID NO:1:

```
CTCAAAAGGG GCCGGATTTC CTTCTCCTGG AGGCAGATGT TGCCTCTCTC TCTCGCTCGG      60

ATTGGTTCAG TGCACTCTAG AAACACTGCT GTGGTGGAGA AACTGGACCC CAGGTCTGGA     120

GCGAATTCCA GCCTGCAGGG CTGATAAGCG AGGCATTAGT GAGATTGAGA GAGACTTTAC     180

CCCGCCGTGG TGGTTGGAGG GCGCGCAGTA GAGCAGCAGC ACAGGCGCGG GTCCCGGGAG     240

GCCGGCTCTG CTCGCGCCGA G ATG TGG AAT CTC CTT CAC GAA ACC GAC TCG      291
                         Met Trp Asn Leu Leu His Glu Thr Asp Ser
                          1               5                  10

GCT GTG GCC ACC GCG CGC CGC CCG CGC TGG CTG TGC GCT GGG GCG CTG      339
Ala Val Ala Thr Ala Arg Arg Pro Arg Trp Leu Cys Ala Gly Ala Leu
             15                  20                  25

GTG CTG GCG GGT GGC TTC TTT CTC CTC GGC TTC CTC TTC GGG TGG TTT      387
Val Leu Ala Gly Gly Phe Phe Leu Leu Gly Phe Leu Phe Gly Trp Phe
         30                  35                  40

ATA AAA TCC TCC AAT GAA GCT ACT AAC ATT ACT CCA AAG CAT AAT ATG      435
Ile Lys Ser Ser Asn Glu Ala Thr Asn Ile Thr Pro Lys His Asn Met
     45                  50                  55

AAA GCA TTT TTG GAT GAA TTG AAA GCT GAG AAC ATC AAG AAG TTC TTA      483
Lys Ala Phe Leu Asp Glu Leu Lys Ala Glu Asn Ile Lys Lys Phe Leu
 60                  65                  70

TAT AAT TTT ACA CAG ATA CCA CAT TTA GCA GGA ACA GAA CAA AAC TTT      531
Tyr Asn Phe Thr Gln Ile Pro His Leu Ala Gly Thr Glu Gln Asn Phe
 75                  80                  85                  90

CAG CTT GCA AAG CAA ATT CAA TCC CAG TGG AAA GAA TTT GGC CTG GAT      579
Gln Leu Ala Lys Gln Ile Gln Ser Gln Trp Lys Glu Phe Gly Leu Asp
                 95                 100                 105

TCT GTT GAG CTA GCA CAT TAT GAT GTC CTG TTG TCC TAC CCA AAT AAG      627
Ser Val Glu Leu Ala His Tyr Asp Val Leu Leu Ser Tyr Pro Asn Lys
            110                 115                 120

ACT CAT CCC AAC TAC ATC TCA ATA ATT AAT GAA GAT GGA AAT GAG ATT      675
Thr His Pro Asn Tyr Ile Ser Ile Ile Asn Glu Asp Gly Asn Glu Ile
        125                 130                 135

TTC AAC ACA TCA TTA TTT GAA CCA CCT CCT CCA GGA TAT GAA AAT GTT      723
Phe Asn Thr Ser Leu Phe Glu Pro Pro Pro Pro Gly Tyr Glu Asn Val
    140                 145                 150

TCG GAT ATT GTA CCA CCT TTC AGT GCT TTC TCT CCT CAA GGA ATG CCA      771
Ser Asp Ile Val Pro Pro Phe Ser Ala Phe Ser Pro Gln Gly Met Pro
155                 160                 165                 170

GAG GGC GAT CTA GTG TAT GTT AAC TAT GCA CGA ACT GAA GAC TTC TTT      819
Glu Gly Asp Leu Val Tyr Val Asn Tyr Ala Arg Thr Glu Asp Phe Phe
                175                 180                 185

AAA TTG GAA CGG GAC ATG AAA ATC AAT TGC TCT GGG AAA ATT GTA ATT      867
Lys Leu Glu Arg Asp Met Lys Ile Asn Cys Ser Gly Lys Ile Val Ile
            190                 195                 200

GCC AGA TAT GGG AAA GTT TTC AGA GGA AAT AAG GTT AAA AAT GCC CAG      915
Ala Arg Tyr Gly Lys Val Phe Arg Gly Asn Lys Val Lys Asn Ala Gln
        205                 210                 215

CTG GCA GGG GCC AAA GGA GTC ATT CTC TAC TCC GAC CCT GCT GAC TAC      963
Leu Ala Gly Ala Lys Gly Val Ile Leu Tyr Ser Asp Pro Ala Asp Tyr
    220                 225                 230

TTT GCT CCT GGG GTG AAG TCC TAT CCA GAT GGT TGG AAT CTT CCT GGA     1011
Phe Ala Pro Gly Val Lys Ser Tyr Pro Asp Gly Trp Asn Leu Pro Gly
235                 240                 245                 250
```

-continued

```
GGT GGT GTC CAG CGT GGA AAT ATC CTA AAT CTG AAT GGT GCA GGA GAC      1059
Gly Gly Val Gln Arg Gly Asn Ile Leu Asn Leu Asn Gly Ala Gly Asp
                255                 260                 265

CCT CTC ACA CCA GGT TAC CCA GCA AAT GAA TAT GCT TAT AGG CGT GGA      1107
Pro Leu Thr Pro Gly Tyr Pro Ala Asn Glu Tyr Ala Tyr Arg Arg Gly
            270                 275                 280

ATT GCA GAG GCT GTT GGT CTT CCA AGT ATT CCT GTT CAT CCA ATT GGA      1155
Ile Ala Glu Ala Val Gly Leu Pro Ser Ile Pro Val His Pro Ile Gly
        285                 290                 295

TAC TAT GAT GCA CAG AAG CTC CTA GAA AAA ATG GGT GGC TCA GCA CCA      1203
Tyr Tyr Asp Ala Gln Lys Leu Leu Glu Lys Met Gly Gly Ser Ala Pro
    300                 305                 310

CCA GAT AGC AGC TGG AGA GGA AGT CTC AAA GTG CCC TAC AAT GTT GGA      1251
Pro Asp Ser Ser Trp Arg Gly Ser Leu Lys Val Pro Tyr Asn Val Gly
315                 320                 325                 330

CCT GGC TTT ACT GGA AAC TTT TCT ACA CAA AAA GTC AAG ATG CAC ATC      1299
Pro Gly Phe Thr Gly Asn Phe Ser Thr Gln Lys Val Lys Met His Ile
                335                 340                 345

CAC TCT ACC AAT GAA GTG ACA AGA ATT TAC AAT GTG ATA GGT ACT CTC      1347
His Ser Thr Asn Glu Val Thr Arg Ile Tyr Asn Val Ile Gly Thr Leu
            350                 355                 360

AGA GGA GCA GTG GAA CCA GAC AGA TAT GTC ATT CTG GGA GGT CAC CGG      1395
Arg Gly Ala Val Glu Pro Asp Arg Tyr Val Ile Leu Gly Gly His Arg
        365                 370                 375

GAC TCA TGG GTG TTT GGT GGT ATT GAC CCT CAG AGT GGA GCA GCT GTT      1443
Asp Ser Trp Val Phe Gly Gly Ile Asp Pro Gln Ser Gly Ala Ala Val
    380                 385                 390

GTT CAT GAA ATT GTG AGG AGC TTT GGA ACA CTG AAA AAG GAA GGG TGG      1491
Val His Glu Ile Val Arg Ser Phe Gly Thr Leu Lys Lys Glu Gly Trp
395                 400                 405                 410

AGA CCT AGA AGA ACA ATT TTG TTT GCA AGC TGG GAT GCA GAA GAA TTT      1539
Arg Pro Arg Arg Thr Ile Leu Phe Ala Ser Trp Asp Ala Glu Glu Phe
                415                 420                 425

GGT CTT CTT GGT TCT ACT GAG TGG GCA GAG GAG AAT TCA AGA CTC CTT      1587
Gly Leu Leu Gly Ser Thr Glu Trp Ala Glu Glu Asn Ser Arg Leu Leu
            430                 435                 440

CAA GAG CGT GGC GTG GCT TAT ATT AAT GCT GAC TCA TCT ATA GAA GGA      1635
Gln Glu Arg Gly Val Ala Tyr Ile Asn Ala Asp Ser Ser Ile Glu Gly
        445                 450                 455

AAC TAC ACT CTG AGA GTT GAT TGT ACA CCG CTG ATG TAC AGC TTG GTA      1683
Asn Tyr Thr Leu Arg Val Asp Cys Thr Pro Leu Met Tyr Ser Leu Val
    460                 465                 470

CAC AAC CTA ACA AAA GAG CTG AAA AGC CCT GAT GAA GGC TTT GAA GGC      1731
His Asn Leu Thr Lys Glu Leu Lys Ser Pro Asp Glu Gly Phe Glu Gly
475                 480                 485                 490

AAA TCT CTT TAT GAA AGT TGG ACT AAA AAA AGT CCT TCC CCA GAG TTC      1779
Lys Ser Leu Tyr Glu Ser Trp Thr Lys Lys Ser Pro Ser Pro Glu Phe
                495                 500                 505

AGT GGC ATG CCC AGG ATA AGC AAA TTG GGA TCT GGA AAT GAT TTT GAG      1827
Ser Gly Met Pro Arg Ile Ser Lys Leu Gly Ser Gly Asn Asp Phe Glu
            510                 515                 520

GTG TTC TTC CAA CGA CTT GGA ATT GCT TCA GGC AGA GCA CGG TAT ACT      1875
Val Phe Phe Gln Arg Leu Gly Ile Ala Ser Gly Arg Ala Arg Tyr Thr
        525                 530                 535

AAA AAT TGG GAA ACA AAC AAA TTC AGC GGC TAT CCA CTG TAT CAC AGT      1923
Lys Asn Trp Glu Thr Asn Lys Phe Ser Gly Tyr Pro Leu Tyr His Ser
    540                 545                 550

GTC TAT GAA ACA TAT GAG TTG GTG GAA AAG TTT TAT GAT CCA ATG TTT      1971
Val Tyr Glu Thr Tyr Glu Leu Val Glu Lys Phe Tyr Asp Pro Met Phe
```

-continued

```
                   555                 560                 565                 570
AAA TAT CAC CTC ACT GTG GCC CAG GTT CGA GGA GGG ATG GTG TTT GAG                 2019
Lys Tyr His Leu Thr Val Ala Gln Val Arg Gly Gly Met Val Phe Glu
                575                 580                 585

CTA GCC AAT TCC ATA GTG CTC CCT TTT GAT TGT CGA GAT TAT GCT GTA                 2067
Leu Ala Asn Ser Ile Val Leu Pro Phe Asp Cys Arg Asp Tyr Ala Val
                590                 595                 600

GTT TTA AGA AAG TAT GCT GAC AAA ATC TAC AGT ATT TCT ATG AAA CAT                 2115
Val Leu Arg Lys Tyr Ala Asp Lys Ile Tyr Ser Ile Ser Met Lys His
                605                 610                 615

CCA CAG GAA ATG AAG ACA TAC AGT GTA TCA TTT GAT TCA CTT TTT TCT                 2163
Pro Gln Glu Met Lys Thr Tyr Ser Val Ser Phe Asp Ser Leu Phe Ser
            620                 625                 630

GCA GTA AAG AAT TTT ACA GAA ATT GCT TCC AAG TTC AGT GAG AGA CTC                 2211
Ala Val Lys Asn Phe Thr Glu Ile Ala Ser Lys Phe Ser Glu Arg Leu
635                 640                 645                 650

CAG GAC TTT GAC AAA AGC AAC CCA ATA GTA TTA AGA ATG ATG AAT GAT                 2259
Gln Asp Phe Asp Lys Ser Asn Pro Ile Val Leu Arg Met Met Asn Asp
                655                 660                 665

CAA CTC ATG TTT CTG GAA AGA GCA TTT ATT GAT CCA TTA GGG TTA CCA                 2307
Gln Leu Met Phe Leu Glu Arg Ala Phe Ile Asp Pro Leu Gly Leu Pro
            670                 675                 680

GAC AGG CCT TTT TAT AGG CAT GTC ATC TAT GCT CCA AGC AGC CAC AAC                 2355
Asp Arg Pro Phe Tyr Arg His Val Ile Tyr Ala Pro Ser Ser His Asn
            685                 690                 695

AAG TAT GCA GGG GAG TCA TTC CCA GGA ATT TAT GAT GCT CTG TTT GAT                 2403
Lys Tyr Ala Gly Glu Ser Phe Pro Gly Ile Tyr Asp Ala Leu Phe Asp
700                 705                 710

ATT GAA AGC AAA GTG GAC CCT TCC AAG GCC TGG GGA GAA GTG AAG AGA                 2451
Ile Glu Ser Lys Val Asp Pro Ser Lys Ala Trp Gly Glu Val Lys Arg
715                 720                 725                 730

CAG ATT TAT GTT GCA GCC TTC ACA GTG CAG GCA GCT GCA GAG ACT TTG                 2499
Gln Ile Tyr Val Ala Ala Phe Thr Val Gln Ala Ala Ala Glu Thr Leu
                735                 740                 745

AGT GAA GTA GCC TAAGAGGATT CTTTAGAGAA TCCGTATTGA ATTTGTGTGG                     2551
Ser Glu Val Ala
            750

TATGTCACTC AGAAAGAATC GTAATGGGTA TATTGATAAA TTTTAAAATT GGTATATTTG               2611

AAATAAAGTT GAATATTATA TATAAAAAAA AAAAAAAAA AA                                   2653
```

(2) INFORMATION FOR SEQ ID NO:2:

(i) SEQUENCE CHARACTERISTICS:
        (A) LENGTH: 750 amino acids
        (B) TYPE: amino acid
        (D) TOPOLOGY: linear (ii) MOLECULE TYPE: protein (xi) SEQUENCE DESCRIPTION: SEQ ID NO:2:

```
Met Trp Asn Leu Leu His Glu Thr Asp Ser Ala Val Ala Thr Ala Arg
 1               5                  10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
```

```
                65                  70                  75                  80
Pro His Leu Ala Gly Thr Glu Gln Asn Phe Gln Leu Ala Lys Gln Ile
                        85                  90                  95
Gln Ser Gln Trp Lys Glu Phe Gly Leu Asp Ser Val Glu Leu Ala His
                100                 105                 110
Tyr Asp Val Leu Leu Ser Tyr Pro Asn Lys Thr His Pro Asn Tyr Ile
                115                 120                 125
Ser Ile Ile Asn Glu Asp Gly Asn Glu Ile Phe Asn Thr Ser Leu Phe
            130                 135                 140
Glu Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
                180                 185                 190
Lys Ile Asn Cys Ser Gly Lys Ile Val Ile Ala Arg Tyr Gly Lys Val
            195                 200                 205
Phe Arg Gly Asn Lys Val Lys Asn Ala Gln Leu Ala Gly Ala Lys Gly
        210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
        275                 280                 285
Leu Pro Ser Ile Pro Val His Pro Ile Gly Tyr Tyr Asp Ala Gln Lys
    290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
                340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
        370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
                420                 425                 430
Glu Trp Ala Glu Glu Asn Ser Arg Leu Leu Gln Glu Arg Gly Val Ala
            435                 440                 445
Tyr Ile Asn Ala Asp Ser Ser Ile Glu Gly Asn Tyr Thr Leu Arg Val
        450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
```

-continued

```
Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapiens
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:3:

```
Ser Leu Tyr Glu Ser Xaa Thr Lys
1               5
```

(2) INFORMATION FOR SEQ ID NO:4:

```
    (i) SEQUENCE CHARACTERISTICS:
        (A) LENGTH: 15 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapiens
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:4:

Xaa Tyr Pro Asp Gly Xaa Asn Leu Pro Gly Gly Xaa Val Gln Arg
1               5                   10                  15

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:5:

Phe Tyr Asp Pro Met Phe Lys
1               5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: double
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:6:

Ile Tyr Asn Val Ile Gly Thr Leu Lys
1               5
```

```
(2) INFORMATION FOR SEQ ID NO:7:

(i) SEQUENCE CHARACTERISTICS:
         (A) LENGTH: 22 amino acids
         (B) TYPE: amino acid
         (C) STRANDEDNESS: double
         (D) TOPOLOGY: linear (ii) MOLECULE TYPE: peptide (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:7:

Phe Leu Tyr Xaa Xaa Thr Gln Ile Pro His Leu Ala Gly Thr Glu Gln
1               5                  10                  15

Asn Phe Gln Leu Ala Lys
            20

(2) INFORMATION FOR SEQ ID NO:8:

(i) SEQUENCE CHARACTERISTICS:
         (A) LENGTH: 17 amino acids
         (B) TYPE: amino acid
         (C) STRANDEDNESS: double
         (D) TOPOLOGY: linear (ii) MOLECULE TYPE: peptide (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:8:

Gly Val Ile Leu Tyr Ser Asp Pro Ala Asp Tyr Phe Ala Pro Asp Val
1               5                  10                  15

Lys (2) INFORMATION FOR SEQ ID NO:9:

(i) SEQUENCE CHARACTERISTICS:
         (A) LENGTH: 17 amino acids
         (B) TYPE: amino acid
         (C) STRANDEDNESS: double
         (D) TOPOLOGY: linear (ii) MOLECULE TYPE: peptide (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen
```

```
        (xi) SEQUENCE DESCRIPTION: SEQ ID NO:9:

Pro Val Ile Leu Tyr Ser Asp Pro Ala Asp Tyr Phe Ala Pro Gly Val
1               5                   10                  15

Lys (2) INFORMATION FOR SEQ ID NO:10:

(i) SEQUENCE CHARACTERISTICS:
         (A) LENGTH: 15 amino acids
         (B) TYPE: amino acid
         (C) STRANDEDNESS: double
         (D) TOPOLOGY: linear (ii) MOLECULE TYPE: peptide (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:10:

Ala Phe Ile Asp Pro Leu Gly Leu Pro Asp Arg Pro Phe Tyr Arg
1               5                   10                  15

(2) INFORMATION FOR SEQ ID NO:11:

(i) SEQUENCE CHARACTERISTICS:
         (A) LENGTH: 19 amino acids
         (B) TYPE: amino acid
         (C) STRANDEDNESS: double
         (D) TOPOLOGY: linear (ii) MOLECULE TYPE: peptide (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:11:

Tyr Ala Gly Glu Ser Phe Pro Gly Ile Tyr Asp Ala Leu Phe Asp Ile
1               5                   10                  15

Glu Ser Lys (2) INFORMATION FOR SEQ ID NO:12:

(i) SEQUENCE CHARACTERISTICS:
         (A) LENGTH: 22 amino acids
         (B) TYPE: amino acid
         (C) STRANDEDNESS: double
         (D) TOPOLOGY: linear (ii) MOLECULE TYPE: peptide (iii) HYPOTHETICAL: NO (iv) ANTI-SENSE: NO
```

(vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:12:

Thr Ile Leu Phe Ala Ser Xaa Asp Ala Glu Glu Phe Gly Xaa Xaa Xaa
1               5                   10                  15

Ser Thr Glu Glu Ala Glu
            20

(2) INFORMATION FOR SEQ ID NO:13:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:13:

TTYTAYGAYC CNATGTT                                              17

(2) INFORMATION FOR SEQ ID NO:14:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:14:

AACATNGGRT CRTARAA                                              17

(2) INFORMATION FOR SEQ ID NO:15:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:15:

ATHTAYAAYG TNATHGG                                                      17

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:16:

CCDATNACRT TRTADAT                                                      17

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:17:

CCNGCNGAYT AYTTYGC                                                      17

(2) INFORMATION FOR SEQ ID NO:18:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO

```
        (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:18:

GCRAARTART CNGCNGG                                                        17

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:19:

ACNGARCARA AYTTYCARCT                                                     20

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:20:

AGYTGRAART TYTGYTCNGT                                                     20

(2) INFORMATION FOR SEQ ID NO:21:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO
```

```
        (vi) ORIGINAL SOURCE:
             (A) ORGANISM: Homo sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:21:

GARCARAAYT TYCARCT                                                      17

(2) INFORMATION FOR SEQ ID NO:22:

(i) SEQUENCE CHARACTERISTICS:
             (A) LENGTH: 17 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:22:

AGYTGRAART TYTGYTC                                                      17

(2) INFORMATION FOR SEQ ID NO:23:

(i) SEQUENCE CHARACTERISTICS:
             (A) LENGTH: 20 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:23:

TGGGAYGCNG ARGARTTYGG                                                   20

(2) INFORMATION FOR SEQ ID NO:24:

(i) SEQUENCE CHARACTERISTICS:
             (A) LENGTH: 20 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO
```

-continued (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:24:

CCRAAYTCYT CNGCRTCCCA                                                            20

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:25:

TGGGAYGCNG ARGARTT                                                                17

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:26:

AAYTCYTCNG CRTCCCA                                                                17

(2) INFORMATION FOR SEQ ID NO:27:

(i) SEQUENCE CHARACTERISTICS:
        (A) LENGTH: 780 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

```
TACACTTATC CCATTCGGAC ATGCCCACCT TGGAACTGGA GACCCTTACA CCCCAGGCTT      60

CCCTTCGTTC AACCACACCC ANNNGTTTCC ACCAGTTGAA TCTTCAGGAC TACCCCACAT     120

TGCTGTTCAG ACCATCTCTA GCAGTGCAGC AGCCAGGCTG TTCAGCAAAA TGGATGGAGA     180

CACATGCTCT GANAGNNGTT GGAAAGGTGC GATCCANNNT TCCTGTAAGG TNNGACNNAA     240

CAAAGCAGGA GANNNNGCCA GANTAATGGT GAAACTAGAT GTGAACAATT CCATGAAAGA     300

CAGGAAGATT CTGAACATCT TCGGTGCTAT CCAGGGATTT GAAGAACCTG ATCGGTATGT     360

TGTGATTGGA GCCCAGAGAG ACTCCTGGGG CCCAGGAGTG GCTAAAGCTG GCACTGGAAC     420

TGCTATATTG TTGGAACTTG CCCGTGTGAT CTCAGACATA GTGAAAAACG AGGGCTACAA     480

ACCGAGGCGA AGCATCATCT TTGCTAGCTG GAGTGCAGGA GACTACGGAG CTGTGGGTGC     540

TACTGAATGG CTGGAGGGGT ACTCTGCCAT GCTGCATGCC AAAGCTTTCA CTTACATCAN     600

NGCTTGGATG CTCCAGTCCT GGGAGCAAGC CATGTCAAGA TTTCTGCCAG CCCCTTGCTG     660

TATATGCTGC TGGGGAGTAT TATGAAGGGG GTGAAGAATC CAGCAGCAGT CTCAGAGAGC     720

NNNNCTCTAT AACAGACTTG GCCCAGACTG GGTAAAAGCA GTTGTTCCTC TTGGCCTGGA     780
```

(2) INFORMATION FOR SEQ ID NO:28:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

```
TGCAGAAAAG CTATTCAAAA ACATGGAAGG AAACTGTCCT CCTAGTTGGA ATATAGATTC      60

CTCATGTAAG CTGGAACTTT CACAGAATCA AAATGTGAAG CTCACTGTGA ACAATGTACT     120

GAAAGAAACA AGAATACTTA ACATCTTTGG CGTTATTAAA GGCTATGAGG AACCAGACCG     180

CTACATTGTA GTAGGAGCCC AGAGAGACGC TTGGGGCCCT GGTNGTTGCG AAGTCCAGTG     240

TGGGAACAGG TCTTNCTGTT GAAACTTGCC CAAGTATTCT CAGATATGAT TTCAAAAGAT     300

GGATTTAGAC CCAGCAGGAG TATTATCTTT GCCAGCTGGA CTGCAGGAGA CTATGGAGCT     360

GTTGGTCCGA CTGAGTGGCT GGAGGGGTAC CTTTCATCTT TGCATCTAAA GNNNGCTTTC     420

ACTTACATTA ATNCTGGATA AAGTCGTCCT GGGTACTAGC AACTTCAAGG TTTCTGCCAG     480

CCCCCTATTA TATACACTTA TGGGAAGAT AATGCAGGAN NCGTAAAGCA TCCGANNNNN     540

NNNTTGATGG AAAATATCTA TATCGAAACA GTAATTGGAT TAGCAAAATT GAGGAACTTT     600

CCTTGGACAA TGCTGCATTC CCTTTTCTTG CATATTCAGG AATCCCAGCA GTTTCTTTCT     660
```

(2) INFORMATION FOR SEQ ID NO:29:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:29:

TATGGAAGGA GACTGTCCCT CTGACTGGAA AACAGACTCT ACATGTAGGA TGGTAACCTC    60

AGAAAGCAAG AATGTGAAGC TCACTGTGAG CAATGTGCTG AAAGAGATAA AAATTCTTAA   120

CATCTTTGGA GTTATTAAAG GCTTTGTAGA ACCAGATCAC TATGTTGTAG TTGGGGCCCA   180

GAGAGATGCA TGGGGCCCTG GAGCTGCAAA ATCNCGGTGT AGGCACAGCT CTCCTATTGA   240

AACTTGCCCA GATGTTCTCA GATATGGTCT TAAAAGATGG GTTTCAGCCC AGCAGAAGCA   300

TTATCTTTGC CAGTTGGAGT GCTGGAGACT TTGGATCGGT TGGTGCCACT GAATGGCTAG   360

AGGGATACCT TTCGTCNCCT GCATTTAAAG GCTTTCACTT ATATTAATCT GGATAAAGCG   420

GTTCTTGGTA CCAGCAACTT CAAGGTTTCT GCCAGCCCAC TGTTGTATAC GCTTATTGAG   480

AAAACAATGC AAAATGTGAA GCATCCGGTT ACTGGGCAAT TTCTATATCA GGACAGCAAC   540

(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:30:

ACGGAGCAAA ACTTTCAGCT TGCAAAG    27

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Membrane Specific Antigen (xi) SEQUENCE DESCRIPTION: SEQ ID NO:31:

Thr Glu Gln Asn Phe Gln Leu Ala Lys
1               5

(2) INFORMATION FOR SEQ ID NO:32:

(i) SEQUENCE CHARACTERISTICS:

(A) LENGTH: 36 base pairs
            (B) TYPE: nucleic acid
            (C) STRANDEDNESS: double
            (D) TOPOLOGY: linear (ii) MOLECULE TYPE: peptide (iii) HYPOTHETICAL: NO (iv) ANTI-SENSE: NO (vi) ORIGINAL SOURCE:
            (A) ORGANISM: Homo Sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:32:

CTCTTCGGCA TCCCAGCTTG CAAACAAAAT TGTTCT                                      36

(2) INFORMATION FOR SEQ ID NO:33:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: peptide (iii) HYPOTHETICAL: NO (iv) ANTI-SENSE: NO (vi) ORIGINAL SOURCE:
            (A) ORGANISM: Homo Sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:33:

AGAACAATTT TGTTTGCAAG CTGGGATGCC AAGGAG                                      36

(2) INFORMATION FOR SEQ ID NO:34:

(i) SEQUENCE CHARACTERISTICS:
            (A) LENGTH: 12 amino acids
            (B) TYPE: amino acid
            (C) STRANDEDNESS: double
            (D) TOPOLOGY: linear (ii) MOLECULE TYPE: peptide (iii) HYPOTHETICAL: NO (iv) ANTI-SENSE: NO (vi) ORIGINAL SOURCE:
            (A) ORGANISM: Homo Sapien
            (G) CELL TYPE: Carcinoma (vii) IMMEDIATE SOURCE:
            (B) CLONE: Prostate Specific Membrane Antigen (xi) SEQUENCE DESCRIPTION: SEQ ID NO:34:

Arg Thr Ile Leu Phe Ala Ser Trp Asp Ala Glu Glu
1                5                  10

(2) INFORMATION FOR SEQ ID NO:35:

(i) SEQUENCE CHARACTERISTICS:

```
        (A) LENGTH: 6 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (G) CELL TYPE: Carcinoma (vii) IMMEDIATE SOURCE:
        (B) CLONE: Prostate Specific Membrane Antigen (xi) SEQUENCE DESCRIPTION: SEQ ID NO:35:

Asp Glu Leu Lys Ala Glu
1               5

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (G) CELL TYPE: Carcinoma (vii) IMMEDIATE SOURCE:
        (B) CLONE: Prostate Specific Membrane Antigen (xi) SEQUENCE DESCRIPTION: SEQ ID NO:36:

Asn Glu Asp Gly Asn Glu
1               5

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (G) CELL TYPE: Carcinoma (vii) IMMEDIATE SOURCE:
        (B) CLONE: Prostate Specific Membrane Antigen (xi) SEQUENCE DESCRIPTION: SEQ ID NO:37:

Lys Ser Pro Asp Glu Gly
1               5

(2) INFORMATION FOR SEQ ID NO:38:
```

```
    (i) SEQUENCE CHARACTERISTICS:
        (A) LENGTH: 17 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (G) CELL TYPE: Carcinoma (vii) IMMEDIATE SOURCE:
        (B) CLONE: Prostate Specific Membrane Antigen (xi) SEQUENCE DESCRIPTION: SEQ ID NO:38:

Ala Gly Ala Leu Val Leu Ala Gly Gly Phe Phe Leu Leu Gly Phe Leu
1               5                  10                  15

Phe
```

PROSTATE-SPECIFIC MEMBRANE ANTIGEN

"This application is a continuation application of U.S. Ser. No. 08/325,553, filed Oct. 18, 1994, now U.S. Pat. No. 5,538,866, which is a continuation of U.S. Ser. No. 07/973,337, filed Nov. 5, 1992, now abandoned, the contents of which are hereby incorporated by reference."

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citation for these references may be is found at the end of this application, preceding the sequence listing and the claims.

The prostate gland is a site of significant pathology affected by conditions such as benign growth (BPH) neoplasia (prostatic cancer) and infection (prostatitis). Prostate cancer represents the second leading cause of death from cancer in man (1). However prostatic cancer is the leading site for cancer development in men. The difference between these two facts relates to prostatic cancer occurring with increasing frequency as men age, especially in the ages beyond 60 at a time when death from other factors often intervenes. Also, the spectrum of biologic aggressiveness of prostatic cancer is great, so that in some men following detection the tumor remains a latent histologic tumor and does not become clinically significant, whereas in other it progresses rapidly, metastasizes and kills the man in a relatively short 2–5 year period (1, 2).

In prostate cancer cells, two specific proteins that are made in very high concentrations are prostatic acid phosphatase (PAP) and prostate specific antigen (PSA) (3, 4, 5). These proteins have been characterized and have been used to follow response to therapy. With the development of cancer, the normal architecture of the gland becomes altered, including loss of the normal duct structure for the removal of secretions and thus the secretions reach the serum. Indeed measurement of serum PSA is suggested as a potential screening method for prostatic cancer. Indeed, the relative amount of PSA and/or PAP in the cancer reduces as compared to normal or benign tissue.

PAP was one of the earliest serum markers for detecting metastatic spread (3). PAP hydrolyses tyrosine phosphate and has a broad substrate specificity. Tyrosine phosphorylation is often increased with oncogenic transformation. It has been hypothesized that during neoplastic transformation there is less phosphatase activity available to inactivate proteins that are activated by phosphorylation on tyrosine residues. In some instances, insertion of phosphatases that have tyrosine phosphatase activity has reversed the malignant phenotype.

PSA is a protease and it is not readily appreciated how loss of its activity correlates with cancer development (4, 5). The proteolytic activity of PSA is inhibited by zinc. Zinc concentrations are high in the normal prostate and reduced in prostatic cancer. Possibly the loss of zinc allows for increased proteolytic activity by PSA. As proteases are involved in metastasis and some proteases stimulate mitotic activity, the potentially increased activity of PSA could be hypothesized to play a role in the tumors metastases and spread (6).

Both PSA and PAP are found in prostatic secretions. Both appear to b dependent on the presence of androgens for their production and are substantially reduced following androgen deprivation.

Prostate-specific membrane antigen (PSM) which appears to be localized to the prostatic membrane has been identified. This antigen was identified as the result of generating monoclonal antibodies to a prostatic cancer cell, LNCaP (7).

Dr. Horoszewicz established a cell line designated LNCaP from the lymph node of a hormone refractory, heavily pretreated patient (8). This line was found to have an aneuploid human male karyotype. It maintained prostatic differentiation functionality in that it produced both PSA and PAP. It possessed an androgen receptor of high affinity and specificity. Mice were immunized with LNCaP cells and hybridomas were derived from sensitized animals. A monoclonal antibody was derived and was designated 7E11-CS (7). The antibody staining was consistent with a membrane location and isolated fractions of LNCaP cell membranes exhibited a strongly positive reaction with immunoblotting and ELISA techniques. This antibody did not inhibit or enhance the growth of LNCaP cells in vitro or in vivo. The antibody to this antigen was remarkably specific to prostatic epithelial cells, as no reactivity was observed in any other component. Immunohistochemical staining of cancerous epithelial cells was more intense than that of normal or benign epithelial cells.

Dr. Horoszewicz also reported detection of immunoreactive material using 7E11-C5 in serum of prostatic cancer patients (7). The immunor activity was detectable in nearly 60% of patients with stage D-2 disease and in a slightly lower percentage of patients with earlier stage disease, but the numbers of patients in the latter group are small. Patients with benign prostatic hyperplasia (BPH) were negative. Patients with no apparent disease were negative, but 50–60% of patients in remission yet with active stable disease or with progression demonstrated positive serum reactivity. Patients with non prostatic tumors did not show immunoreactivity with 7E11-C5.

The 7E11-C5 monoclonal antibody is currently in clinical trials. The aldehyde groups of the antibody were oxidized and the linker-chelator glycol-tyrosyl-(n, ϵ-diethylenetriamine-pentacetic acid)-lysine (GYK-DTPA) was coupled to the reactive aldehydes of the heavy chain (9). The resulting antibody was designated CYT-356. Immunohistochemical staining patterns were similar except that the CYT-356 modified antibody stained skeletal muscle. The comparison of CYT-356 with 7E11-C5 monoclonal antibody suggested both had binding to type 2 muscle fibers. The reason for the discrepancy with the earlier study, which reported skeletal muscle to be negative, was suggested to be due to differences in tissue fixation techniques. Still, the most intense and definite reaction was observed with prostatic epithelial cells, especially cancerous cells. Reactivity with mouse skeletal muscle was detected with immunohistochemistry but not in imaging studies. The Indium[111]-labeled antibody localized to LNCaP tumors grown in nude mice with an uptake of nearly 30% of the injected dose per gram tumor at four days. In-vivo, no selective retention of the antibody was observed in antigen negative tumors such as PC-3 and DU-145, or by skeletal muscle.

Very little was known about th PSM antigen. An effort at purification and characterization has been described at meetings by Dr. George Wright and colleagues (10, 11). These investigators have shown that following electrophoresis on acrylamide gels and Western blotting, the PSM antigen appears to have a molecular weight of 100 kilodaltons (kd). Chemical and enzymatic treatment showed that both the peptide and carbohydrate moieties of the PSM antigen are required for recognition by the 7E11-C-5 monoclonal antibody. Competitive binding studies with specific lectins suggested that galNAc is the dominant carbohydrate of the antigenic epitope.

A 100 kd glycoprotein unique to prostate cells and tissues was purified and characterized. The protein was digested proteolytically with trypsin and nine peptide fragments wire sequenced. Using the technique of degenerate PCR (polymerase chain reaction), the full-length 2.65 kilobase (kb) cDNA coding for this antigen was cloned. Preliminary results have revealed that this antigen is highly expressed in prostate cancer tissues, including bone and lymph node metastases (12). The entire DNA sequence for the cDNA as well as the predicted amino acid sequence for the antigen was determined. Further characterization of the PSM antigen is presently underway in the applicants' laboratory including: analysis of PSM gene expression in a wide variety of tissues, transfection of the PSM gene into cells not expressing the antigen, chromosome localization of the PSM gene, cloning of the genomic PSM gene with analysis of the PSM promoter and generation of polyclonal and monoclonal antibodies against highly antigenic peptide domains of the PSM antigen, and identification of any endogenous PSM binding molecules (ligands).

BRIEF DESCRIPTION OF FIGURES

FIG. 4 100 kD PSM antigen following immunoprecipitation of $^{35}$S-Methionine labelled LNCaP cells with Cyt-356 antibody.

FIG. 5 3% agarose gels stained with Ethidium bromide revealing PCR products obtained using the degenerate PSM antigen primers. The arrow points to sample IN-20, which is a 1.1 kb PCR product which we later confirmed to be a partial cDNA coding for the PSM gene.

FIG. 6 2% agarose gels of plasmid DNA resulting from TA cloning of PCR products. Inserts are excised from the PCR II vector (Invitrogen Corp.) by digestion with EcoRI. 1.1 kb PSM gene partial cDNA product is shown in lane 3 of gel 1.

FIG. 12 Results of PCR of human prostate tissues using PSM gene primers. Lanes ar numbered from left to right. Lane 1, LNCaP; Lane 2, H26; Lane 3, DU-145; Lane 4, Normal Prostate; Lane 5, BPH; Lane 6, Prostate Cancer; Lane 7, BPH; Lane 8, Normal; Lane 9, BPH; Lane 10, BPH; Lane 11, BPH; Lane 12, Normal; Lane 13, Normal; Lane 14, Cancer; Lane 15, Cancer; Lane 16, Cancer; Lane 17, Normal; Lane 18, Cancer; Lane 19, IN-20 Control; Lane 20, PSM cDNA FIG. 13 Isoelectric point of PSM antigen (non-glycosylated)

Figure 14:
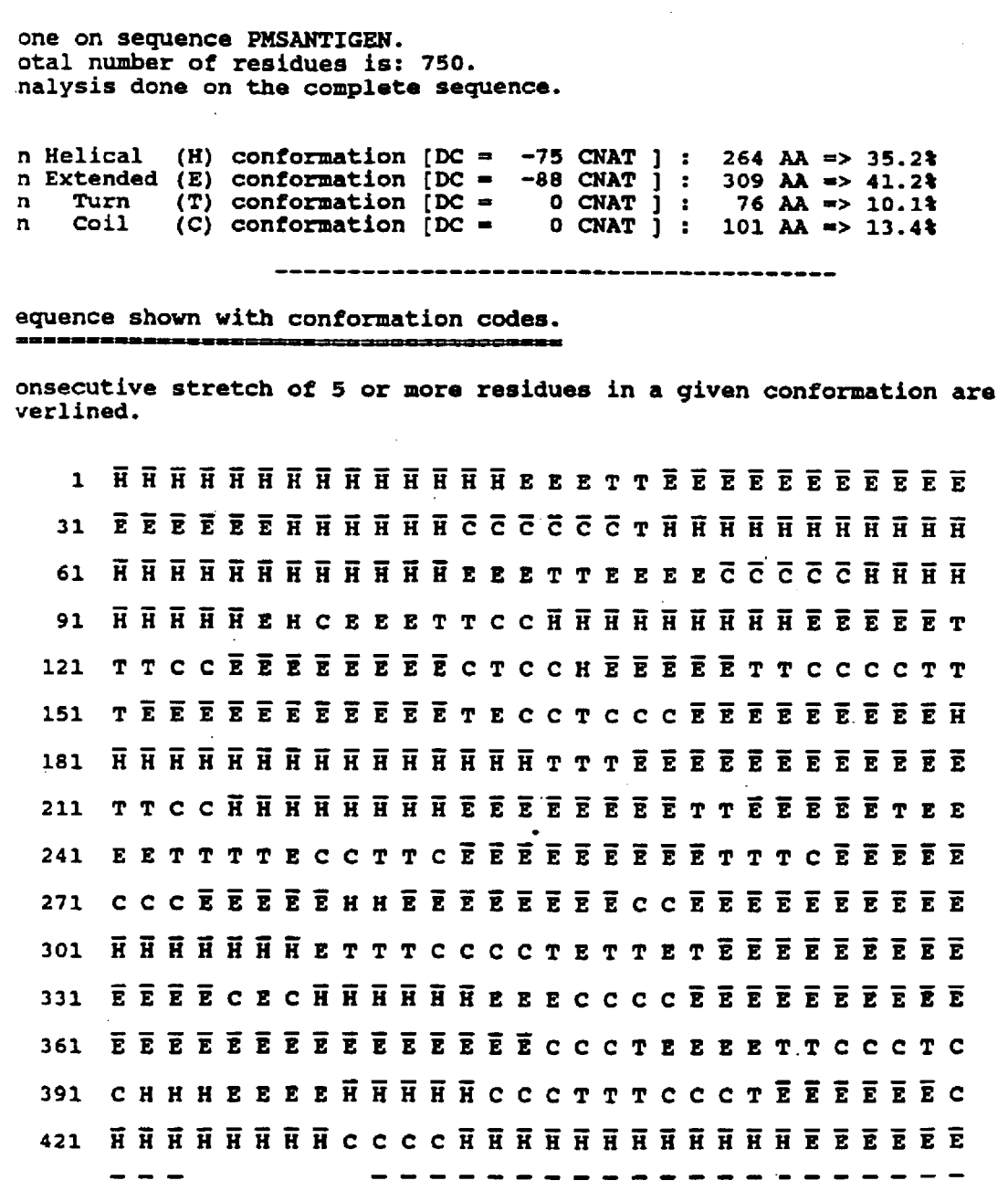
Figure 14:
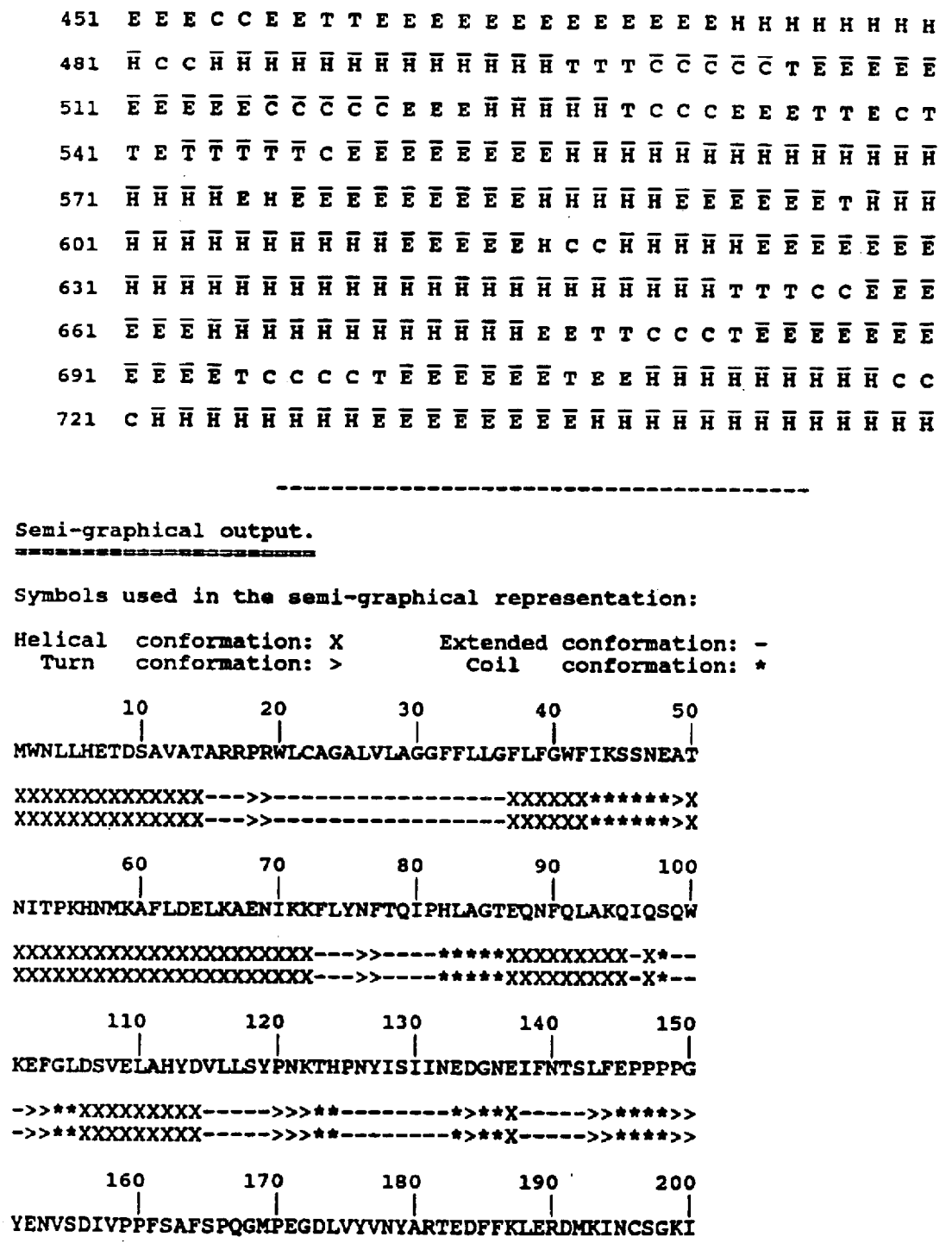

FIG. 14: Secondary structure of PSM antigen (SEQ ID NO:2).

FIG. 16: Homology of PSMA antigen (SEQ ID NO:1) with chicken (SEQ ID NO:27), rat (SEQ ID NO:28) and human (SEQ ID NO:29) transferrin receptor sequence.

SUMMARY OF THE INVENTION

Figure 1:
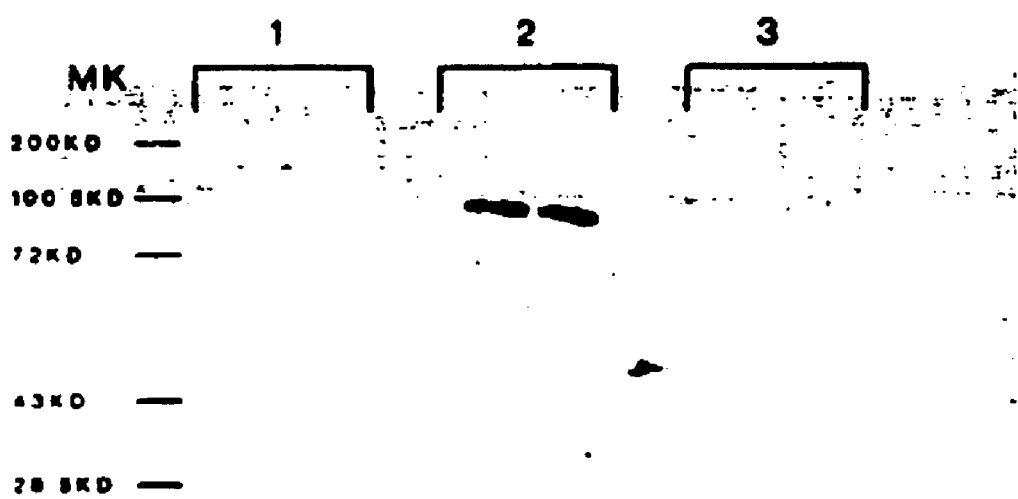
FIG. 1 Signal in lane 2 represent the 100 kD PSM antigen. The EGFr was used as the positive control and is shown in lane 1. Incubation with rabbit antimouse (RAM) antibody alone served as negative control and is shown in lane 3.

This invention provides an isolated mammalian nucleic acid molecule encoding a mammalian prostate-specific membrane (PSM) antigen. The isolated mammalian nucleic acid may be DNA, cDNA or RNA.

This invention also provides nucleic acid molecule comprising a nucleic acid molecule of at least 15 nucleotides capable of specifically hybridizing with a sequence included within the sequence of a nucleic acid molecule encoding the PSM antigen. The nucleic acid molecule may either be DNA or RNA.

This invention provides nucleic acid molecule of at least 15 nucleotides capable of specifically hybridizing with a sequence of a nucleic acid molecule which is complementary to the nucleic acid molecule encoding a mammalian prostate-specific membrane antigen.

This invention further provides a method of detecting expression of the PSM antigen which comprises obtaining total mRNA from the cell and contacting the mRNA so obtained with a labelled PSM antigen specific nucleic acid molecule under hybridizing conditions, determining the presence of mRNA hybridized to the probe, and thereby detecting the expression of the PSM antigen by the cell. The PSM antigen in tissue sections may be similarly detected.

This invention provides isolated nucleic acid sequence of PSM antigen operatively linked to a promoter of RNA transcription. This invention further provides a vector which comprises an isolated mammalian nucleic acid molecule of PSM antigen.

This invention further provides a host vector system for the production of a polypeptide having the biological activity of a mammalian PSM antigen which comprises the vector comprising the mammalian nucleic acid molecule encoding a mammalian PSM antigen and a suitable host. The suitable host for the expression of PSM antigen may be a bacterial cell, insect cell, or mammalian cell.

This invention also provides a method of producing a polypeptide having the biological activity of a mammalian PSM antigen which comprises growing the host cell of vector system having a vector comprising the isolated mammalian nucleic acid molecule encoding a mammalian PSM antigen and a suitable host under suitable conditions permitting production of the polypeptide and recovery of the polypeptide so produced.

This invention provides a method for determining whether a ligand can bind to a mammalian PSM antigen which comprises contacting a mammalian cell having an isolated mammalian DNA molecule encoding a mammalian PSM antigen with the ligand under conditions permitting binding of ligands to the mammalian PSM antigen, and determining whether the ligand binds to a mammalian PSM antigen. This invention further provides ligands which bind to PSM antigen.

This invention provides purified mammalian PSM antigen. This invention also provides a polypeptide encoded by the isolated mammalian nucleic acid molecule encoding a mammalian PSM antigen. This invention further provides a method to identify and purify ligands of mammalian PSM antigen.

This invention further provides a method to produce both polyclonal and monoclonal antibody using purified PSM antigens or polypeptides encoded by an isolated mammalian nucleic acid molecule encoding a mammalian PSM antigen.

This invention provides polyclonal and monoclonal antibody most likely but not limited to directed either to peptide Asp-Glu-Leu-Lys-Ala-Glu (SEQ ID No. 35), or Asn-Glu-Asp-Gly-Asn-Glu (SEQ ID No. 36) or Lys-Ser-Pro-Asp-Glu-Gly (SEQ ID No. 37) of the PSM antigen.

This invention provides a therapeutic agent comprising an antibody directed against a mammalian PSM antigen and a cytotoxic agent conjugated thereto.

This invention also provides a method of imaging prostate cancer in human patients which comprises administering to the patient at least one antibody directed against PSM antigen, capable of binding to the cell surface of the prostate cancer cell and labeled with an imaging agent under conditions so as to form a complex between the monoclonal antibody and the cell surface PSM antigen. This invention further provides a composition comprising an effective imaging amount of the antibody directed against PSM antigen and a pharmaceutically acceptable carrier.

This invention further provides a method of imaging prostate cancer in human patients which comprises administering to the patient multiple antibodies directed towards different PSM epitopes.

The invention also provides-a method of imaging prostate cancer in human patients which comprises administering to the patient at least one ligand, capable of binding to the cell surface of the prostate cancer cell and labelled with an imaging agent under conditions so as to form a complex between the ligand and the cell surface PSM antigen. This invention further provides a composition comprising an effective imaging amount of PSM antigen and a pharmaceutically acceptable carrier.

This invention provides an immunoassay for measuring the amount of the PSM antigen in a biological sample, e.g. serum, comprising steps of a) contacting the biological sample with at least one PSM antibody to form a complex with said antibody and the PSM antigen, and b) measuring the amount of PSM antigen in said biological sample by measuring the amount of said complex.

This invention also provides an immunoassay for measuring the amount of the PSM antigen in a biological sample comprising steps of a) contacting the biological sample with at least one PSM ligand to form a complex with said ligand and the PSM antigen, and b) measuring the amount of the PSM antigen in said biological sample by measuring the amount of said complex.

This invention provides a method to purify mammalian PSM antigen comprising steps of:

a) coupling the antibody directed against PSM antigen to a solid matrix; b) incubating the coupled antibody of a) with a cell lysate containing PSM antigen under the condition permitting binding of the antibody and PSM antigen; c) washing the coupled solid matrix to eliminate impurities and d) eluting the PSM antigen from the bound antibody.

This invention further provides transgenic nonhuman mammals which comprises an isolated nucleic acid molecule of PSM antigen. This invention also provides a transgenic nonhuman mammal whose genome comprises antisense DNA complementary to DNA encoding a mammalian PSM antigen so placed as to be transcribed into antisense mRNA complementary to mRNA encoding the PSM antigen and which hybridizes to mRNA encoding the PSM antigen thereby reducing its translation.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

C=cytosine A=adenosine

T=thymidine G=guanosine

This invention provides an isolated mammalian nucleic acid encoding a mammalian prostate-specific membrane (PSM) antigen.

This invention further provides an isolated mammalian DNA molecule of an isolated mammalian nucleic acid molecule encoding a mammalian prostate-specific membrane antigen. This invention also provides an isolated mammalian cDNA molecule encoding a mammalian prostate-specific membrane antigen. This invention provides an isolated mammalian RNA molecule encoding a mammalina prostate-specific membrane antigen.

In the preferred embodiment of this invention, the isolated nucleic sequence is cDNA from human as shown in sequence ID number 1. This human sequence was submitted to GenBank (Los Alamos National Laboratory, Los Alamos, N.Mex.) with Accession Number, M99487 and the description as PSM, Homo sapiens, 2653 base-pairs.

This invention also encompasses DNAs and cDNAs which encode amino acid sequences which differ from those of PSM antigen, but which should not produce phenotypic changes. Alternatively, this invention also encompasses DNAs and cDNAs which hybridize to the DNA and cDNA of the subject invention. Hybridization methods ar well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated mammalian nucleic acid molecules encoding a mammalian prostate-specific membrane antigen are useful for the development of probes to study the tumorigenesis of prostate cancer.

This invention also provides nucleic acid molecules of at least 15 nucleotides capable of specifically hybridizing with a sequence of a nucleic acid molecule encoding the prostate-specific membrane antigen.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a nucleic acid molecule encoding the prostate-specific membrane antigen can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes PSM antigen into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the PSM antigen molecule downstream of a bacteriophage promoter such as T3, T7 or SP6. Large amounts of RNA probe may be produced by incubating the labeled nucleotides with the linearized PSM antigen fragment where it contains an upstream promoter in the presence of the appropriate RNA polymerase.

This invention also provides a nucleic acid molecule of at least 15 nucleotides capable of specifically hybridizing with a sequence of a nucleic acid molecule which is complementary to the mammalian nucleic acid molecule encoding a mammalian prostate-specific membrane antigen. This molecule may either be a DNA or RNA molecule.

The current invention further provides a method of Detecting the expression of a mammalian PSM antigen expression in a cell which comprises obtaining total mRNA from the cell, contacting the mRNA so obtained with a labelled nucleic acid molecule of at least 15 nucleotides capable of specifically hybridizing with a sequence of the nucleic acid molecule encoding a mammalian PSM antigen under hybridizing conditions, determining the presence of mRNA hybridized to the molecule and thereby detecting the expression of the mammalian prostate-specific membrane antigen in the cell. The nucleic acid molecules synthesized above may be used to detect expression of a PSM antigen by detecting the presence of mRNA coding for the PSM antigen. Total mRNA from the cell may be isolated by many procedures well known to a person of ordinary skill in the art. The hybridizing conditions of the labelled nucleic acid molecules may be determined by routine experimentation well known in the art. The presence of mRNA hybridized to the probe may be determined by gel electrophoresis or other methods known in the art. By measuring th amount of the hybrid made, the expression of the PSM antigen by the cell can be determined. The labelling may be radioactive. For an example, one or more radioactive nucleotides can be incorporated in the nucleic acid when it is made.

In one embodiment of this invention, nucleic acids are extracted by precipitation from lysed cells and the mRNA is isolated from the extract using an oligo-dT column which binds the poly-A tails of the mRNA molecules (13). The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention further provides another method to detect expression of a PSM antigen in tissue sections which comprises contacting the tissue sections with a labelled nucleic acid molecule of at least 15 nucleotides capable of specifically hybridizing with a sequence of nucleic acid molecules encoding a mammalian PSM antigen under hybridizing conditions, determining the presence of mRNA hybridized to the molecule and thereby detecting the expression of the mammalian PSM antigen in tissue sections. The probes are also useful for in-situ hybridization or in order to locate tissues which express this gene, or for other hybridization assays for the presence of this gene or its mRNA in various biological tissues. The in-situ hybridization using a labelled nucleic acid molecule is well known in the art. Essentially, tissue sections are incubated with the labelled nucleic acid molecule to allow the hybridization to occur. The molecule will carry a marker for the detection because it is "labelled", the amount of the hybrid will be determined based on the detection of the amount of the marker and so will the expression of PSM antigen.

This invention further provides isolated PSM antigen nucleic acid molecule operatively linked to a promoter of RNA transcription. The isolated PSM antigen sequence can be linked to vector systems. Various vectors including plasmid vectors, cosmid vectors, bacteriophage vectors and other viruses are well known to ordinary skilled practitioners. This invention further provides a vector which comprises the isolated nucleic acid molecule encoding for the PSM antigen.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the PSM sequence is cloned in the Not I/Sal I site of pSPORT/vector (Gibco®—BRL). This plasmid, p55A-PSM, was deposited on Aug. 14, 1992 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, p55A-PSM, was accorded ATCC Accession Number 75294.

This invention further provides a host vector system for the production of a polypeptide having the biological activity of the prostate-specific membrane antigen. These vectors may be transformed into a suitable host cell to form a host cell vector system for the production of a polypeptide having the biological activity of PSM antigen.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (14). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the PSM antigen.

This invention further provides an isolated DNA or cDNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention further provides a method of producing a polypeptide having the biological activity of the prostate-specific membrane antigen which comprising growing host cells of a vector system containing the PSM antigen sequence under suitable conditions permitting product ion of the polypeptide and recovering the polypeptide so produced.

This invention provides a mammalian cell comprising a DNA molecule encoding a mammalian PSM antigen, such as a mammalian cell comprising a plasmid adapted for expression in a mammalian cell, which comprises a DNA molecule encoding a mammalian PSM antigen and the regulatory elements necessary for expression of the DNA in the mammalian cell so located relative to the DNA encoding the mammalian PSM antigen as to permit expression thereof.

Numerous mammalian cells may be used as hosts, including, but not limited to, the mouse fibroblast cell NIH3T3, CHO cells, HéLa cells, Ltk⁻ cells, Cos cells, etc. Expression plasmids such as that described supra may be used to transfect mammalian cells by methods well known in the art such as calcium phosphate precipitation, electroporation or DNA encoding the mammalian PSM antigen may be otherwise introduced into mammalian cells, e.g., by microinjection, to obtain mammalian cells which comprise DNA, e.g., cDNA or a plasmid, encoding a mammalian PSM antigen.

This invention provides a method for determining whether a ligand can bind to a mammalian prostate-specific membrane antigen which comprises contacting a mammalian cell comprising an isolated DNA molecule encoding a mammalian prostate-specific membrane antigen with the ligand under conditions permitting binding of ligands to the mammalian prostate-specific membrane antigen, and thereby determining whether the ligand binds to a mammalian prostate-specific membrane antigen.

This invention further provides ligands bound to the mammalian PSM antigen.

This invention also provides a therapeutic agent comprising a ligand identified by the above-described method and a cytotoxic agent conjugated thereto. The cytotoxic agent may either be a radioisotope or a toxin. Examples of radioisotopes or toxins are well known to one of ordinary skill in the art.

This invention also provides a method of imaging prostate cancer in human patients which comprises administering to the patients at least one ligand identified by the above-described method, capable of binding to the cell surface of the prostate cancer cell and labelled with an imaging agent under conditions permitting formation of a complex between the ligand and the cell surface PSM antigen. This invention further provides a composition comprising an effective imaging agent of the PSM antigen ligand and a pharmaceutically acceptable carrier. Pharmaceutically acceptable carriers are well known to one of ordinary skill in the art. For an example, such a pharmaceutically acceptable carrier can be physiological saline.

Also provided by this invention is a purified mammalian PSM antigen. As used herein, the term "purified prostate-specific membrane antigen" shall mean isolated naturally-occurring prostate-specific membrane antigen or protein (purified from nature or manufactured such that the primary, secondary and tertiary conformation, and posttranslational modifications ar identical to naturally-occurring material) as well as non-naturally occurring polypeptides having a primary structural conformation (i.e. continuous sequence of amino acid residues). Such polypeptides include derivatives and analogs.

This invention further provides a polypeptide encoded by the isolated mammalian nucleic acid sequence of PSM antigen.

It is believed that there may be natural ligand interacting with the PSM antigen. This invention provides a method to identify such natural ligand or other ligand which can bind to the PSM antigen. A method to identify the ligand comprises a) coupling the purified mammalian PSM antigen to a solid matrix, b) incubating the coupled purified mammalian PSM protein with the potential ligands under the conditions permitting binding of ligands and the purified PSM antigen; c) washing the ligand and coupled purified mammalian PSM antigen complex formed in b) to eliminate the nonspecific binding and impurities and finally d) eluting the ligand from the bound purified mammalian PSM antigen. The techniques of coupling proteins to a solid matrix are well known in the art. Potential ligands may either be deduced from the structure of mammalian PSM or by other empirical experiments known by ordinary skilled practitioners. The conditions for binding may also easily be determined and protocols for carrying such experimentation have long been well documented (15). The ligand-PSM antigen complex will be washed. Finally, the bound ligand will be eluted and characterized. Standard ligands characterization techniques are well known in the art.

The above method may also be used to purify ligands from any biological source. For purification of natural ligands in th cell, cell lysates, serum or other biological samples will be used to incubate with the mammalian PSM antigen bound on a matrix. Specific natural ligand will then be identified and purified as above described.

With the protein sequence information, antigenic areas may be identified and antibodies directed against these areas may be generated and targeted to the prostate cancer for imaging the cancer or therapies.

This invention provides an antibody directed against the amino acid sequence of a mammalian PSM antigen.

This invention provides a method to select specific regions on the PSM antigen to generate antibodies. The protein sequence may be determined from the PSM DNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to mammalian PSM antigen. For an example, hydrophilic sequences of the human PSM antigen shown in hydrophilicity plot of FIG. 15A may be easily selected. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian PSM antigen in living animals, in humans, or in biological tissues or fluids isolated from animals or humans.

In one embodiment, peptides Asp-Glu-Leu-Lys-Ala-Glu (SEQ ID No. 35), Asn-Glu-Asp-Gly-Asn-Glu (SEQ ID No. 36) and Lys-Ser-Pro-Asp-Glu-Gly (SEQ ID No. 37) of human PSM antigen are selected.

This invention further provides polyclonal and monoclonal antibody(ies) against peptides Asp-Glu-Leu-Lys-Ala-Glu (SEQ ID No. 35), Asn-Glu-Asp-Gly-Asn-Glu (SEQ ID No. 36) and Lys-Ser-Pro-Asp-Glu-Gly (SEQ ID No. 37).

This invention provides a therapeutic agent comprising antibodies or ligand(s) directed against PSM antigen and a cytotoxic agent conjugated thereto or antibodies linked enzymes which activate prodrug to kill the tumor. The cytotoxic agent may either be a radioisotope or toxin.

This invention provides a method of imaging prostate cancer in human patients which comprises administering to the patient the monoclonal antibody directed against the peptide of the mammalian PSM antigen capable of binding to the cell surface of the prostate cancer cell and labeled with an imaging agent under conditions permitting formation of a complex between the monoclonal antibody and the cell surface prostate-specific membrane antigen. The imaging agent is a radioisotope such as Indium$^{111}$.

This invention further provides a prostate cancer specific imaging agent comprising the antibody directed against PSM antigen and a radioisotope conjugated thereto.

This invention also provides a composition comprising an effective imaging amount of the antibody directed against the PSM antigen and a pharmaceutically acceptable carrier. The methods to determine effective imaging amounts are well known to a skilled practitioner. One method is by titration using different amounts of the antibody.

This invention further provides an immunoassay for measuring the amount of the prostate-specific membrane antigen in a biological sample comprising steps of a) contacting the biological sample with at least one antibody directed against the PSM antigen to form a complex with said antibody and the prostate-specific membrane antigen, and b) measuring the amount of the prostate-specific membrane antigen in said biological sample by measuring the amount of said complex. One example of the biological sample is a serum sample.

This invention provides a method to purify mammalian prostate-specific membrane antigen comprising steps of a) coupling the antibody directed against the PSM antigen to a solid matrix; b) incubating the coupled antibody of a) with lysate containing prostate-specific membrane antigen under the condition which the antibody and prostate membrane specific can bind; c) washing the solid matrix to eliminate impurities and d) eluting the prostate-specific membrane antigen from the coupled antibody.

This invention also provides a transgenic nonhuman mammal which comprises the isolated nucleic acid molecule encoding a mammalian PSM antigen. This invention further provides a transgenic nonhuman mammal whose genome comprises antisense DNA complementary to DNA encoding a mammalian prostate-specific membrane antigen so placed as to be transcribed into antisense mRNA complementary to mRNA encoding the prostate-specific membrane antigen and which hybridizes to mRNA encoding the prostate specific antigen thereby reducing its translation.

Animal model systems which elucidate the physiological and behavioral roles of mammalian PSM antigen are produced by creating transgenic animals in which the expression of the PSM antigen is either increased or decreased, or the amino acid sequence of the expressed PSM antigen is altered, by a variety of techniques. Examples of these techniques include, but are not limited to: 1) Insertion of normal or mutant versions of DNA encoding a mammalian PSM antigen, by microinjection, electroporation, retroviral transfection or other means well known to those skilled in the art, into appropriate fertilized embryos in order to produce a transgenic animal (16) or 2) Homologous recombination (17) of mutant or normal, human or animal versions of these genes with the native gene locus in transgenic animals to alter the regulation of expression or the structure of these PSM antigen sequences. The technique of homologous recombination is well known in the art. It replaces the native gene with the inserted gene and so is useful for producing an animal that cannot express native PSM antigen but does express, for example, an inserted mutant PSM antigen, which has replaced the native PSM antigen in the animal's genome by recombination, resulting in underexpression of the transporter. Microinjection adds genes to the genome, but does not remove them, and so is useful for producing an animal which expresses its own and added PSM antigens, resulting in overexpression of the PSM antigens.

One means available for producing a transgenic animal, with a mouse as an example, is as follows: Female mice are mated, and the resulting fertilized eggs are dissected out of their oviducts. The eggs are stored in an appropriate medium such as M2 medium (16). DNA or cDNA encoding a mammalian PSM antigen is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Another use of the PSM antigen sequence is to isolate homologous gene or genes in different mammals. The gene or genes can be isolated by low stringency screening of either cDNA or genomic libraries of different mammals using probes from PSM sequence. The positive clones identified will be further analyzed by DNA sequencing techniques which are well known to an ordinary person skilled in the art. For example, the detection of members of the protein serine kinase family by homology probing (18).

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

The approach for cloning the gene involved purification of the antigen in large quantities by immunoprecipitation, and microsequencing of several internal peptides for use in synthesizing degenerate oligonucleotide primers for subsequent use in the polymerase chain reaction (19, 20). A partial cDNA was amplified as a PCR product and this was used as a homologous probe to clone the full-length cDNA molecule from a LNCaP (Lymph Node Carcinoma of Prostate) cell line cDNA plasmid library (8). Early experiments revealed to us that the CYT-356 antibody (9) was not capable of detecting the antigen produced in bacteria since the epitope was the glycosylated portion of the PSM antigen, and this necessitated our more difficult, yet elaborate approach.

I. Western Analysis of the PSM Antigen

Membrane proteins were isolated from cells by hypotonic lysis followed by centrifugation over a sucrose density gradient (21). 10–20 µg of LNCaP, DU-145, and PC-3 membrane proteins were electrophoresed through a 10% SDS-PAGE resolving gel with a 4% stacking gel at 9–10 milliamps for 16–18 hours. Proteins were electroblotted onto PVDF membranes (Millipore® Corp.) in transfer buffer (48 mM Tris base, 39 mM Glycine, 20% Methanol) at 25 volts overnight at 4° C. Membranes were blocked in TSB (0.15 M NaCl, 0.01 M Tris base, 5% BSA) for 30 minutes at room temperature followed by incubation with 10–15 µg/ml of CYT-356 monoclonal antibody (Cytogen Corp.) for 2 hours. Membranes were then incubated with 10–15 µg/ml of rabbit anti-mouse immunoglobulin (Accurate Scientific) for 1 hour at room temperature followed by incubation with $^{125}$I-Protein A (Amersham ) at 1×10$^6$ cpm/ml at room temperature. Membranes were then washed and autoradiographed for 12–24 hours at −70° C. (FIG. 1).

II. Immunohistochemical Analysis of PSM Antigen Expression

The avidin-biotin method of immunohistochemical detection was employed to analyze both human tissue sections and cell lines for PSM Antigen expression (22). Cryostat-cut prostate tissue sections (4–6 µm thick) were fixed in methanollacetone for 10 minutes. Cell cytospins were made on glass slides using 50,000 cells/100 µl/slide. Samples were treated with 1% hydrogen peroxide in PBS for 10–15 minutes in order to remove any endogenous peroxidase activity. Tissue sections were washed several times in PBS, and then incubated with the appropriate suppressor serum for 20 minutes. The suppressor serum was drained off and the sections or cells were then incubated with the diluted CYT-356 monoclonal antibody for 1 hour. Samples were then washed with PBS and sequentially incubated with secondary antibodies (horse or goat immunoglobulins, 1:200 dilution for 30 minutes), and with avidin-biotin complexes (1:25 dilution for 30 minutes). DAB was used as a chromogen, followed by hematoxylin counterstaining and mounting. Frozen sections of prostate samples and duplicate cell cytospins were used as controls for each experiment. As a positive control, the anti-cytokeratin monoclonal antibody CAM 5.2 was used following the same procedure described above. Tissue sections are considered by us to express the PSM antigen if at least 5% of the cells demonstrate immunoreactivity. Our scoring system is as follows: 1=<5%; 2=5–19%; 3=20–75%; and 4>75% positive cells. Homogeneity versus heterogeneity was accounted for by evaluating positive and negative cells in 3–5 high power light microscopic fields (400×), recording the percentage of positive cells among 100–500 cells. The intensity of immunostaining is graded on a 1+ to 4+ scale, where 1+ represents mild, 2–3+ represents moderate, and 4+ represents intense immunostaining as compared to positive controls.

III. Immunoprecipitation of the PSM Antigen

Figure 2:
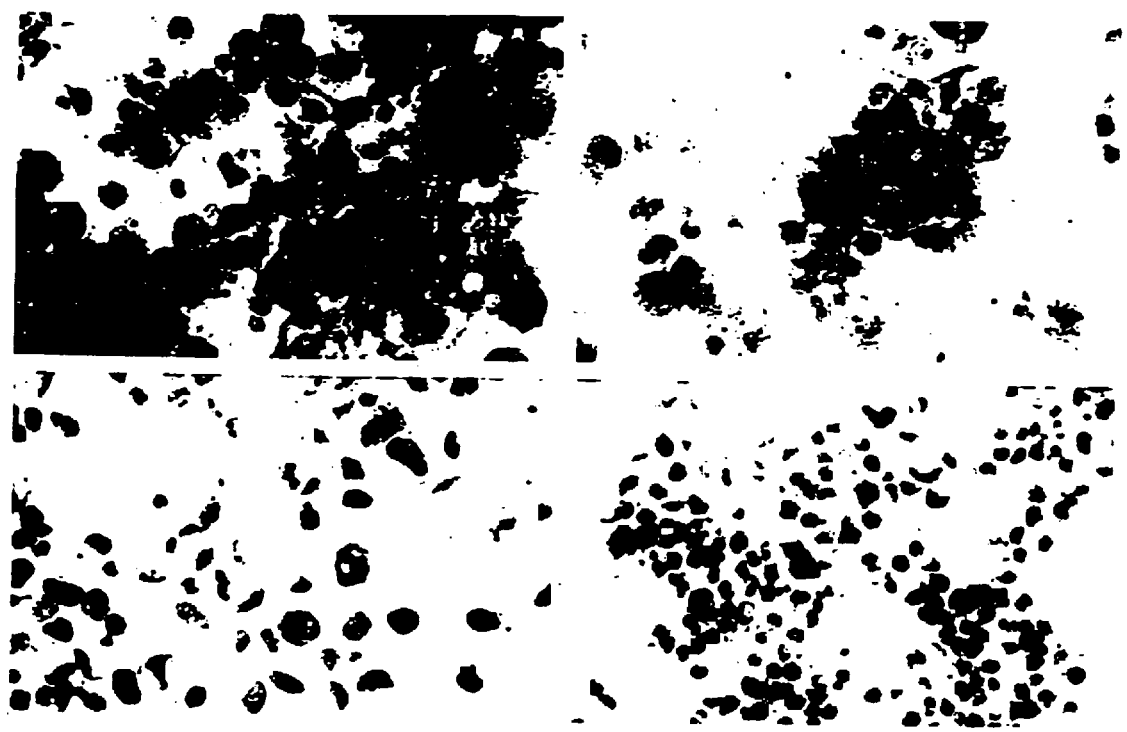
FIG. 2 Upper two photos show LNCaP cytospins staining positively for PSM antigen. Lower left in DU-145 and lower right is PC-3 cytospin, both negative for PSM antigen expression.
Figure 3:
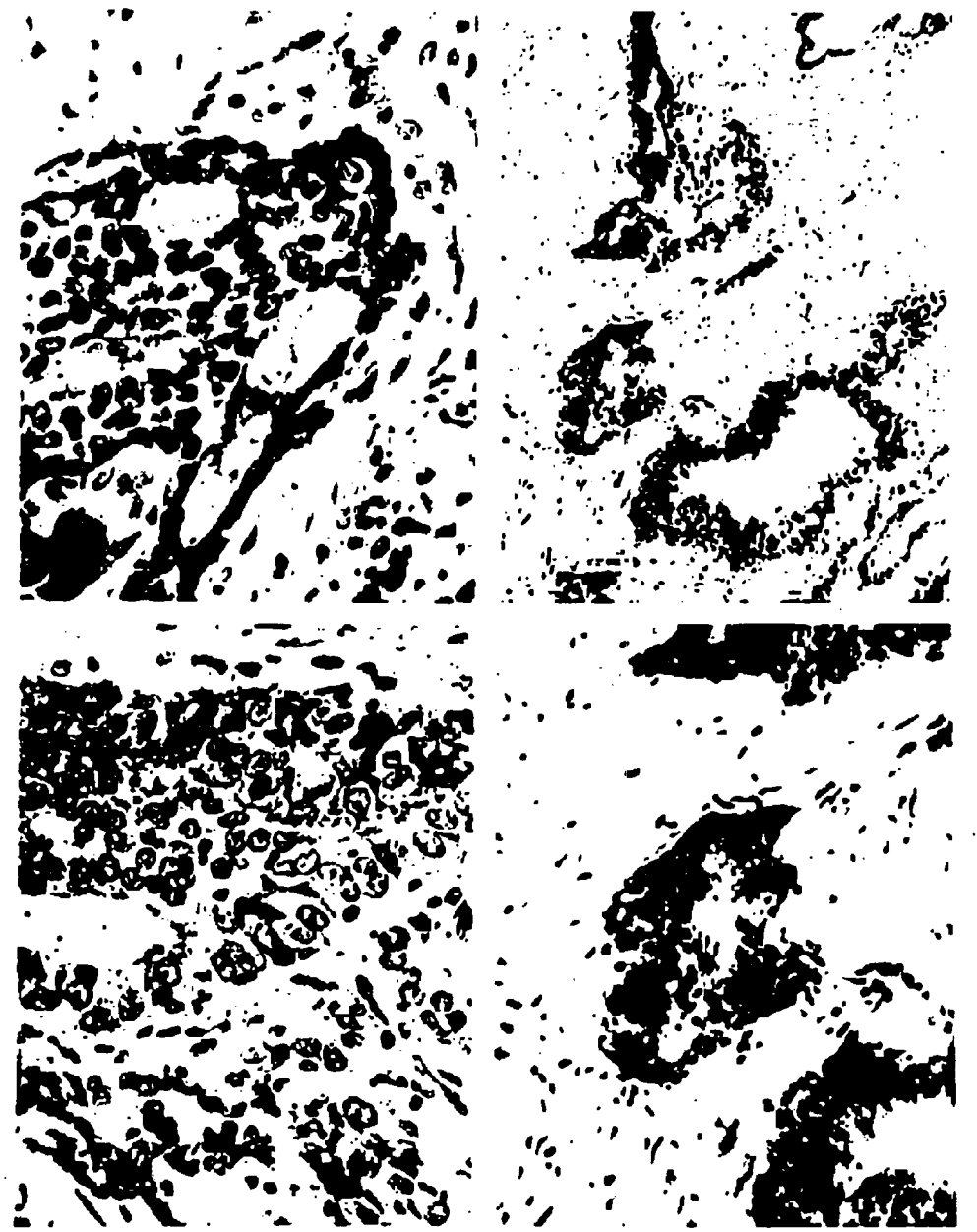
FIG. 3 Upper two panels are human prostate sections (BPH) staining positively for PSM antigen. The lower two panels show invasive prostate carcinoma human sections staining positively for expression of the PSM antigen.
Figure 4:
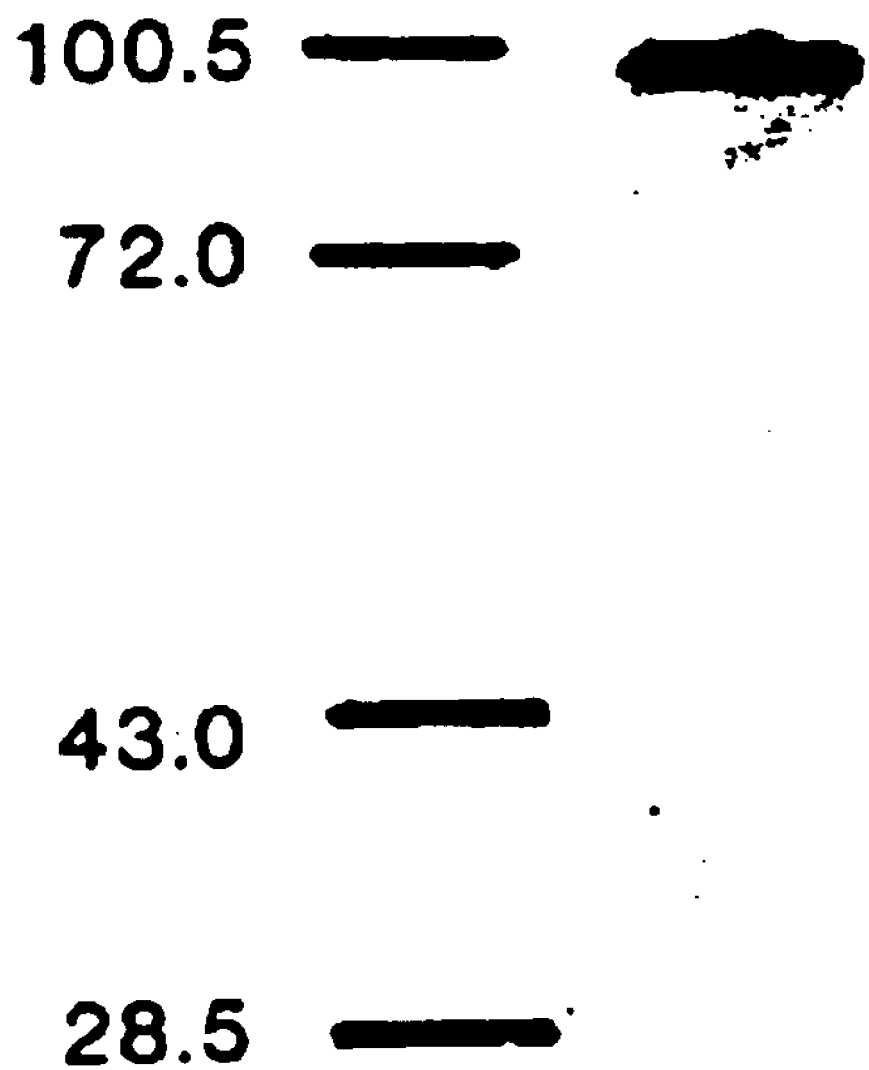

80%-confluent LNCaP cells in 100 mm petri dishes were starved in RPMI media without methionine for 2 hours, after which $^{35}$S-Methionine was added at 100 µCi/ml and the cells were grown for another 16–18 hours. Cells were then washed and lysed by the addition of 1 ml of lysis buffer (1% Triton X-100, 50 mM Hepes pH 7.5, 10% glycerol, 150 mM MgCl$_2$, 1 mM PMSF, and 1 mM EGTA) with incubation for 20 minutes at 4° C. Lysates were pre-cleared by mixing with Pansorbin® cells (Calbiochem®) for 90 minutes at 4° C. Cell lysates were then mixed with Protein A Sepharose® CL-4B beads (Pharmacia®) previously bound with CYT-356 antibody (Cytogen Corp.) and RAM antibody (Accurate Scientific) for 3–4 hours at 4° C. 12 µg of antibody was used per 3 mg of beads per petri dish. Beads were then washed with HNTG buffer (20 mM Hepes pH 7.5, 150 mM NaCl, 0.1% Triton X-100, 10% glycerol, and 2 mM Sodium Orthovanadate), resuspended in sample loading buffer containing β-mercaptoethanol, denatured at 95° C. for 5–10 minutes and run on a 10% SDS-PAGE gel with a 40 stacking gel at 10 milliamps overnight. Gels were stained with Coomassie Blue, destained with acetic acid/methanol, and dried down in a vacuum dryer at 60° C. Gels were then autoradiographed for 16–24 hours at −70° C. (FIG. 2).

IV. Large-Scale Immunoprecipitation and Peptide Sequencing

The procedure described above for immunoprecipitation was repeated with 8 confluent petri dishes containing approximately 6×10$^7$ LNCaP cells. The immunoprecipitation product was pooled and loaded into two lanes of a 10% SDS-PAGE gel and electrophoresed at 9–10 milliamps for 16 hours. Proteins were electroblotted onto Nitrocellulose BA-85 membranes (Schleicher and Schuell®) for 2 hours at 75 volts at 4° C. in transfer buffer. Membranes were stained with Ponceau Red to visualize the proteins and the 100 kD protein band was excised, solubilized, and digested proteolytically with trypsin. HPLC was then performed on the digested sample on an Applied Biosystems Model 171C and clear dominant peptide peaks were selected and sequenced by modified Edman degradation on a modified post liquid Applied Biosystems Model 477A Protein/Peptide Microsequencer (23). Sequencing data on all of the peptides is included within this document. We attempted to sequence the amino-terminus of the PSM antigen by a similar method which involved purifying the antigen by immunoprecipitation and transfer via electroblotting to a PVDF membrane (Millipore®). Protein was analyzed on an Applied Biosystems Model 477A Protein/Peptide Sequencer and the amino terminus was found to be blocked, and therefore no sequence data could be obtained by this technique.

| PSM Antigen Peptide Sequences: | |
|---|---|
| 2T17 #5 | SLYES(W)TK (SEQ ID No. 3) |
| 2T22 #9 | (S)YPDGXNLPGG(g)VQR (SEQ ID No. 4) |
| 2T26 #3 | FYDPMFK (SEQ ID No. 5) |
| 2T27 #4 | IYNVIGTL(K) (SEQ ID No. 6) |
| 2T34 #6 | FLYXXTQIPHLAGTEQNFQLAK (SEQ ID No. 7) |
| 2T35 #2 | G/PVILYSDPADYFAPD/GVK (SEQ ID No. 8, 9) |
| 2T38 #1 | AFIDPLGLPDRPFYR (SEQ ID No. 10) |
| 2T46 #8 | YAGESFPGIYDALFDIESK (SEQ ID No. 11) |
| 2T47 #7 | TILFAS(W)DAEEFGXX(q)STE(e)A(E) . . . (SEQ ID No. 12) |

Notes: X means that no residue could be identified at this position. Capital denotes identification but with a lower degree of confidence. (lower case) means residue present but at very low levels. . . . indicates sequence continues but has dropped below detection limit.

All of these peptide sequences were verified to be unique after a complete homology search of the translated Genbank computer database.

IV. Degenerate PCR

Sense and anti-sense 5'-unphosphorylated degenerate oligonucleotide primers 17 to 20 nucleotides in length corresponding to portions of the above peptides were synthesized on an Applied Biosystems Model 394A DNA Synthesizer. These primers have degeneracies from 32 to 144. The primers used are shown below. The underlined amino acids in the peptides represent the residues used in primer design.

Peptide 3: <u>FYDPMFK</u> (SEQ ID No. 5)

PSM Primer "A" TT(C or T)—TA(C or T)'GA(C or T)—CCX—ATG—TT (SEQ ID No. 13)

PSM Primer "B" AAC—ATX—GG(A or G—TC(A or G)—TA(A or G)—AA (SEQ ID No. 14)

Primer A is sense primer and B is anti-sense. Degeneracy is 32-fold.

Peptide 4: <u>IYNVIGTL</u>(K) (SEQ ID No. 6)

PSM Primer "C" AT(T or C or A)—TA(T or C)—AA(T or C)—GTX AT(T or C or A)—GG (SEQ ID No. 15)

PSM Primer "D" CC(A or T or G)—ATX—AC(G or A) TT(A or TG)—TA(A or G or T)—AT (SEQ ID No. 16)

Primer C is sense primer and D is anti-sense. Degeneracy is 144-told.

Peptide 2: G/PVILYSD<u>PADYFA</u>PD/GVK (SEQ ID No. 8,9)

PSM Primer "E" CCX—GCX—GA(T or C)—TA(T or C)—IT(T or C)—GC (SEQ ID No. 17)

PSM Primer "F" GC(G or A)—AA(A or G)—TA(A or G)—TXC—GCX GG (SEQ ID No. 18)

Primer E is sense primer and F is antisense primer. Degeneracy is 128-fold.

Peptide 6: FLYXXTQIPHLAG<u>TEQNFQ</u>LAK (SEQ ID No. 7)

PSM Primer "I" ACX—A(A or G)—CA(A or G)—AA(T or C)—TT(T or C)—CA(A or G)—CT (SEQ ID No. 19)

PSM Primer "J" AG—(T or C)TG—(A or G)AA—(A or G)TT—(T or C)TG—(T or C)TC—XGT (SEQ ID No. 20)

PSM Primer "K" GA(A or G)—CA(A or G)—AA(T or C)—TT(T or C) CA(A or G)—CT (SEQ ID No. 21)

PSM Primer "L" AG—(T or C)TG—(A or G)AA (A or G)TT—(T or C)TG (T or C)TC (SEQ ID No. 22)

Primers I and K are sense primers and J and L are anti-sense. I and J have degeneracies of 128-fold and K and L have 32-fold degeneracy.

Peptide 7: TILFAS(<u>W)DAEEFG</u>XX(q)STE(e)A(E) . . . (SEQ ID No. 12)

PSM Primer "M" TGG—GA(T or C)—GCX—GA(A or G)—GA(A or G)—TT(C or T)—GG (SEQ ID No. 23)

PSM Primer "N" CC—(G or A)AA—(T or C)TC—(T or C)TC—XGC—(A or G)TC—CCA (SEQ ID No. 24)

PSM Primer "O" TGG—GA(T or C)—GCX—GA(A or G)—GA(A or G)—TT (SEQ ID No. 25)

PSM Primer "P" AA—(T or C)TC—(T or C)TC—XGC—(A or G)TC—CCA (SEQ ID No. 26)

Primers M and O are sense primers and N and P are anti-sense. M and N have degeneracy of 64-fold and O and P are 32-fold degenerate.

Degenerate PCR was performed using a Perkin-Elmer Model 480 DNA thermal cycler. cDNA template for the PCR was prepared from LNCaP mRNA which had been isolated by standard methods of oligo dT chromatography (Collaborative Research). The cDNA synthesis was carried out as follows:

| 4.5 µl | LNCaP poly A+ RNA (2 µg) |
|---|---|
| 1.0 µl | Oligo dT primers (0.5 µg) |
| 4.5 µl | dH$_2$O |
| 10 µl | |

Incubate at 68° C.×10 minutes.
Quick chill on ice×5 minutes.
Add:

| 4 µl | 5 × RT Buffer |
|---|---|
| 2 µl | 0.1M DTT |
| 1 µl | 10 mM dNTPS |
| 0.5 µl | RNasin (Promega) |
| 1.5 µl | dH$_2$O |
| 19 µl | |

Incubate for 2 minutes at 37° C.
Add 1 µl Superscripts Reverse Transcriptase (Gibco®-BRL) Incubate for 1 hour at 37° C.
Add 30 ||l dH$_2$O.
Use 2 µl per PCR reaction.

Degenerate PCR reactions were optimized by varying the annealing temperatures, Mg++ concentrations, primer concentrations, buffer composition, extension times and number of cycles. Our optimal thermal cycler profile was: Denaturation at 94° C.×30 seconds, Annealing at 45–55° C. for 1 minute (depending on the mean T$_m$ of the primers used), and Extension at 72° C. for 2 minutes.

| | |
|---|---|
| 5 µl | 10 × PCR Buffer* |
| 5 µl | 2.5 mM dNTP Mix |
| 5 µl | Primer Mix (containing 0.5–1.0 µg each of sense and anti-sense primers) |
| 5 µl | 100 mM β-mercaptoethanol |
| 2 µl | LNCaP cDNA template |
| 5 µl | 25 mM MgCl$_2$ (2.5 mM final) |
| 21 µl | dH$_2$O |
| 2 µl | diluted Taq Polymerase (0.5 U/µl) |
| 50 µl | total volume |

Tubes were overlaid with 60[1] of light mineral oil and amplified for 30 cycles. PCR products were analyzed by electrophoresing 5µl of each sample on a 2–3% agarose gel followed by staining with Ethidium bromide and photography.

*10×PCR Buffer 166 mM NH$_4$SO$_4$ 670 mM Tris, pH 8.8

2 mg/ml BSA

Figure 5:
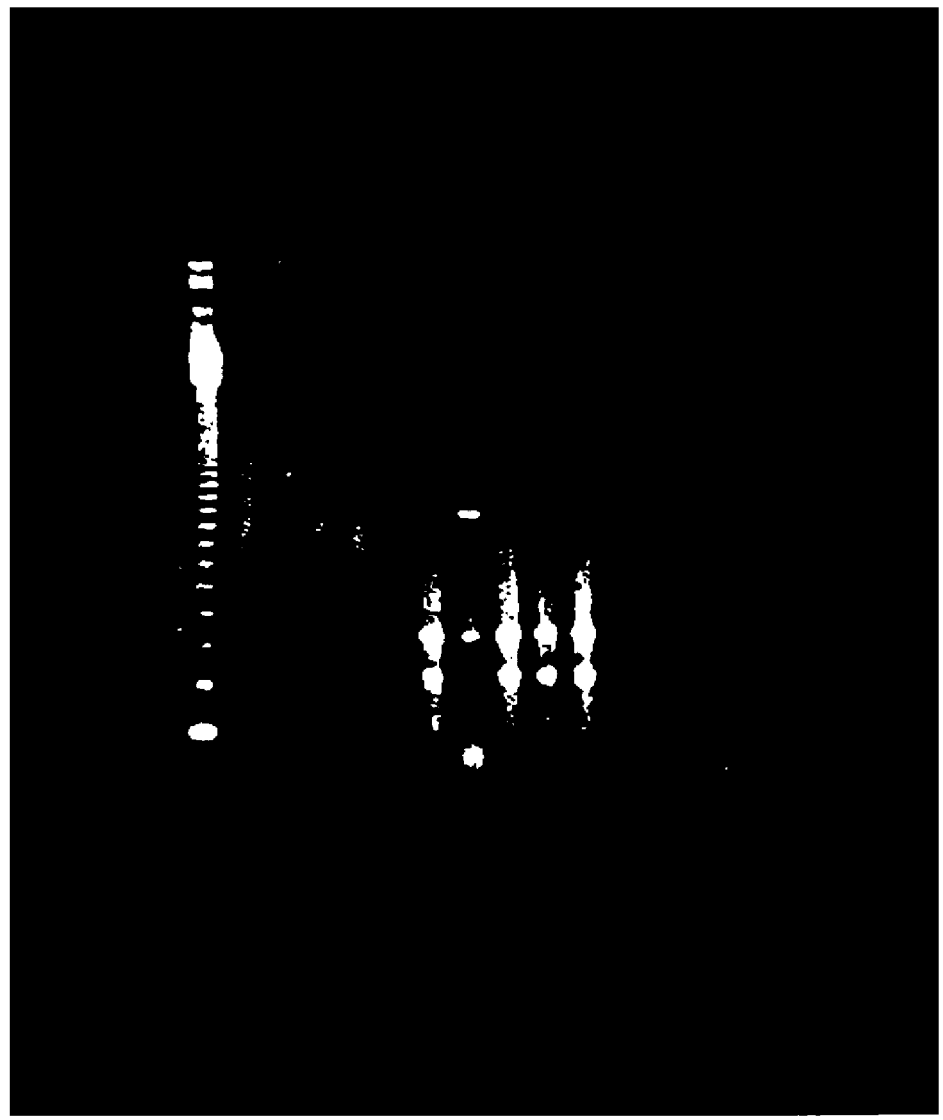

Representative photographs displaying PCR products are shown in FIG. 5.

V. Cloning of PCR Products

Figure 6:

In order to further analyze these PCR products, these products were cloned into a suitable plasmid vector using "TA Cloning" (Invitrogen® Corp.). The cloning strategy employed here is to directly ligate PCR products into a plasmid vector possessing overhanging T residues at the insertion site, exploiting the fact that Taq polymerase leaves overhanging A residues at the ends of the PCR products. The ligation mixes are transformed into competent *E. coli* cells and resulting colonies are grown up, plasmid DNA is isolated by the alkaline lysis method (24), and screened by restriction analysis (FIG. 6).

VI. DNA Sequencing of PCR Products

TA Clones of PCR products were then sequenced by the dideoxy method (25) using Sequenase (U.S. Biochemical). 3–4 µg of each plasmid DNA was denatured with NaOH and ethanol precipitated. Labeling reactions were carried out as per the manufacturers recommendations using 35S-ATP, and th reactions w re terminated as per the same protocol. Sequencing products were then analyzed on 6% polyacrylamide/7M Urea gels using an IBI sequencing apparatus. Gels were run at 120 watts for 2 hours. Following electrophoresis, the gels were fixed for 15–29 minutes in 10% methanol/10% acetic acid, transferred onto Whatman 3MM paper and dried down in a Biorad® vacuum dryer at 80° C. for 2 hours. Gels were then autoradiographed at room temperature for 16–24 hours. In order to determine whether the PCR products were the correct clones, we analyzed the sequences obtained at the 5' and 3' ends of the molecules looking for the correct primer sequences, as well as adjacent sequences which corresponded to portions of the peptides not used in the design of the primers.

IN-20 was confirmed to be correct and represent a partial cDNA for the PSM gene. In this PCR reaction, I and N primers were used. The DNA sequence we obtained when reading from the I primer was:

ACG GAG CAA AAC TTT CAG CT GCA AAG (SEQ ID No. 30)

T E Q N P Q L A K (SEQ ID No. 31)

The underlined amino acids were the portion of peptide 6 that was used to design this sense primer and the remaining amino acids which agree with those present within our peptide confirm that this end of the molecule represents the correct protein (PSM antigen).

When we analyzed the other end of the molecule by reading from the N primer the sequence was:

CTC TTC GGC ATC CCA GCT TGC AAA CAA AAT GT TWCT (SEQ ID No. 32)

Since this represents the anti-sense DNA sequence, we need to show the complementary sense sequence in order to find our peptide.

Sense Sequence:

AGA ACK ATT TTG TTT GCA AGC TGG GAT OCC AAG QAG (SEQ ID No. 33)

R T I L P A S W D A E E (SEQ ID No. 34)

The underlined amino acids here represent the portion of peptide 7 used to create primer N. All of the amino acids upstream of this primer are correct in the IN-20 clone, agreeing with the amino acids found in peptide 7. Further DNA sequencing has enabled us to identify the presence of our other PSM peptides within the DNA sequence of our positive clone.

The DNA sequence of this partial cDNA was found to be unique when screened on the Genbank computer database.

VII. cDNA Library Construction and Cloning of Full-Length PSM cDNA

Figure 7:
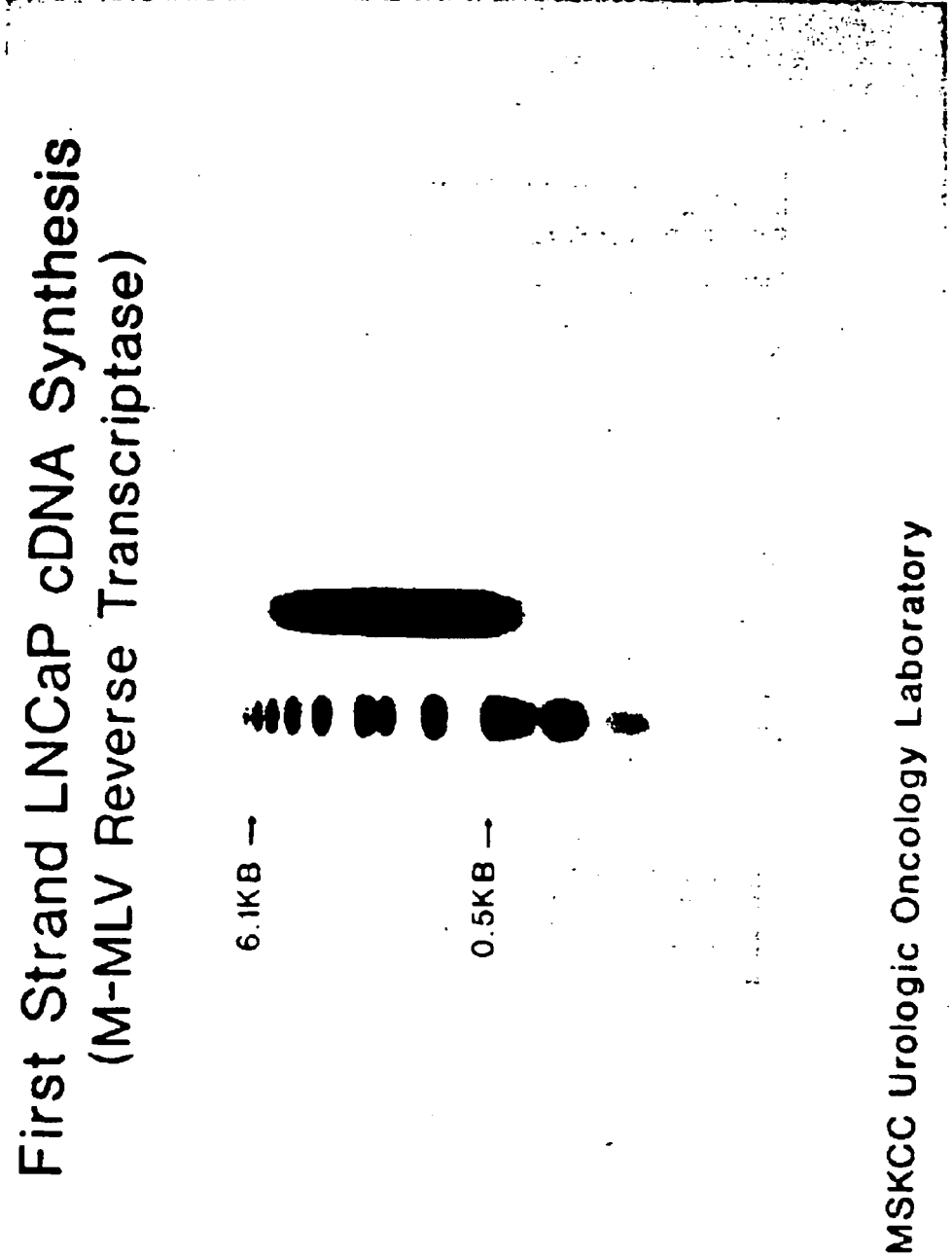
FIG. 7 Autoradiogram showing size of cDNA represented in applicants' LNCaP library.
Figure 8:
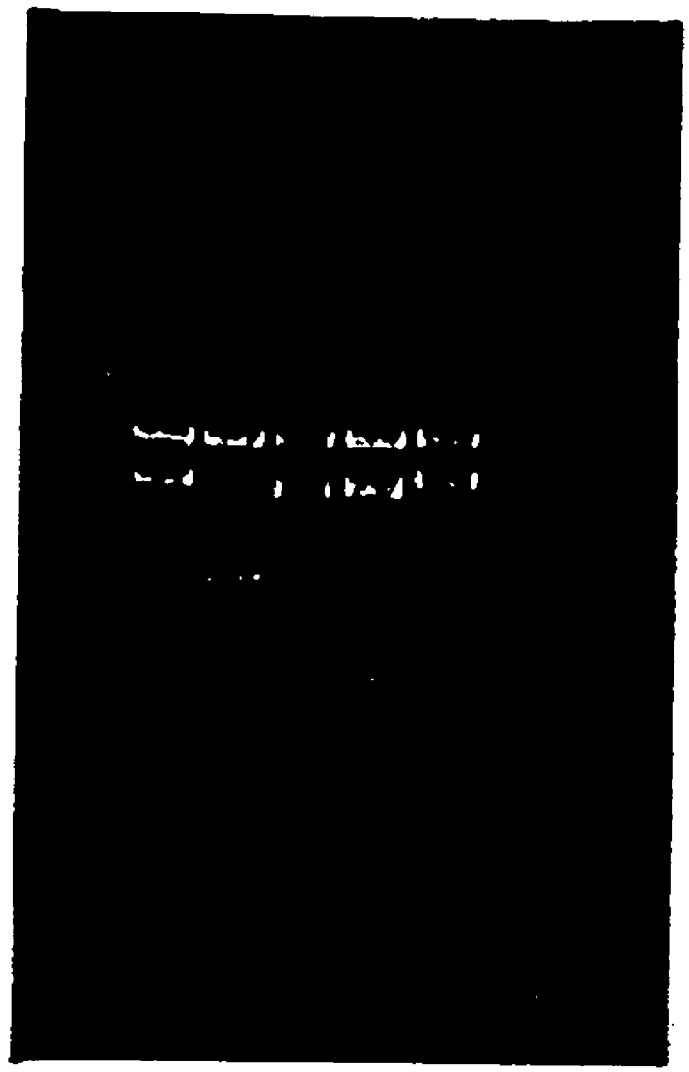
FIG. 8 Restriction analysis of full-length clones of PSM gene obtained after screening cDNA library. Samples have been cut with Not I and Sal I restriction enzymes to liberate the insert.
Figure 9:
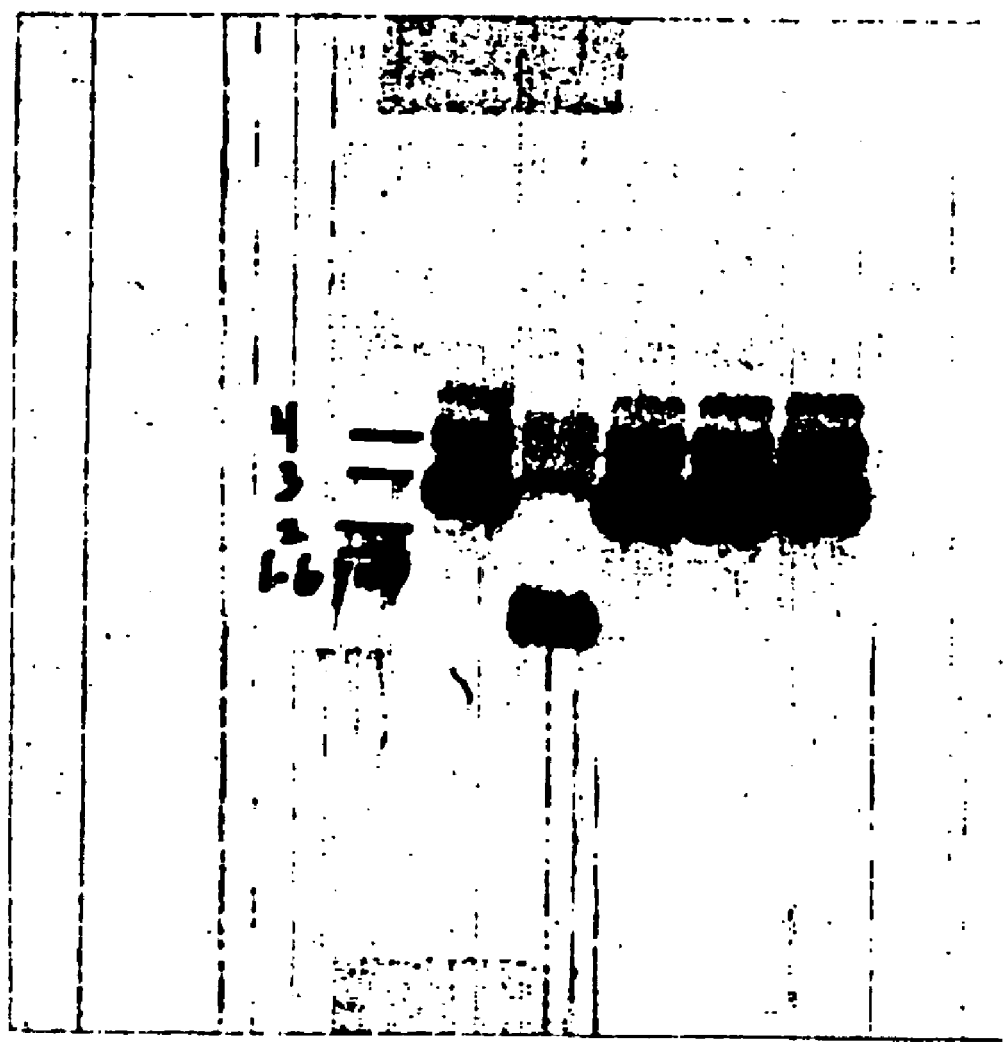
FIG. 9 Plasmid Southern autoradiogram of full length PSM gene clones. Size is approximately 2.7 kb.
Figure 10:
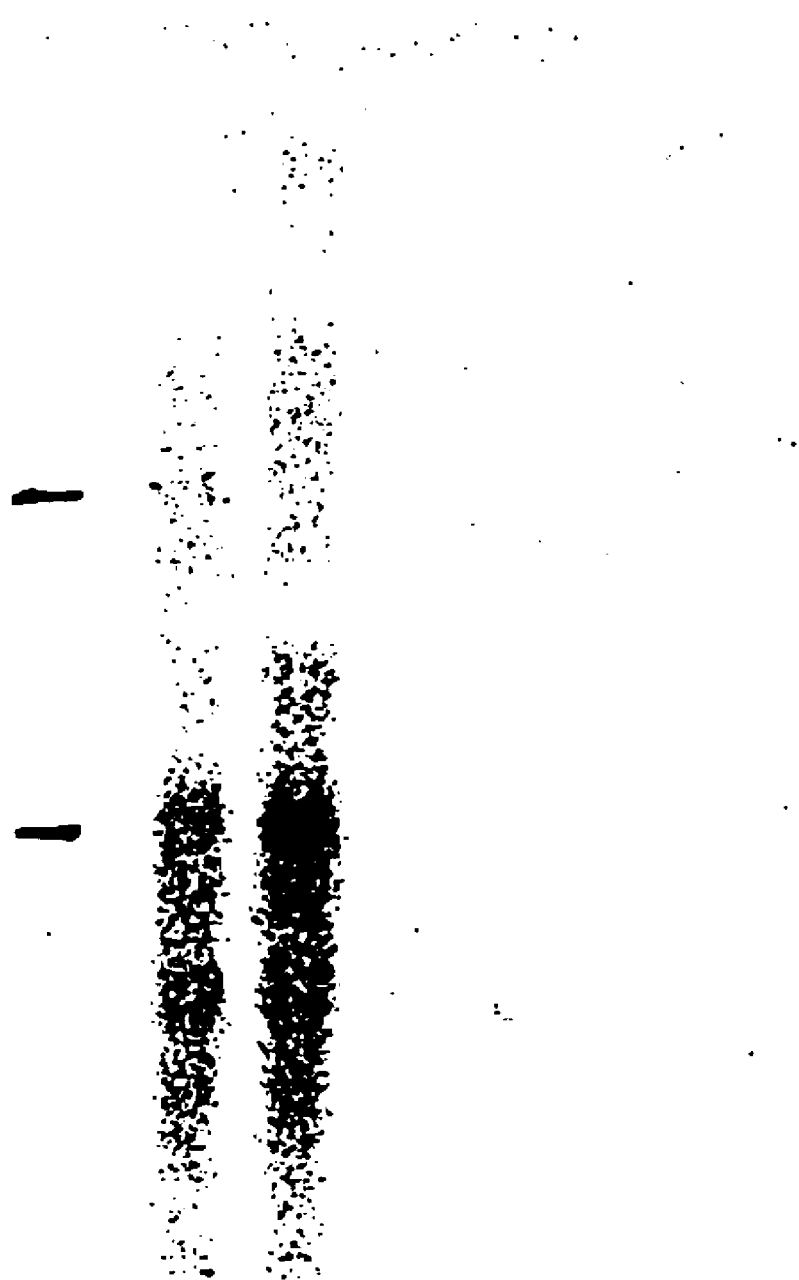
FIG. 10 Northern blot revealing PSM expression limited to LNCaP prostate cancer line and H26 Ras-transfected LNCaP cell line. PC-3, DU-145, T-24, SKRC-27, HELA, MCF-7, HL-60, and others were are all negative.
Figure 11:
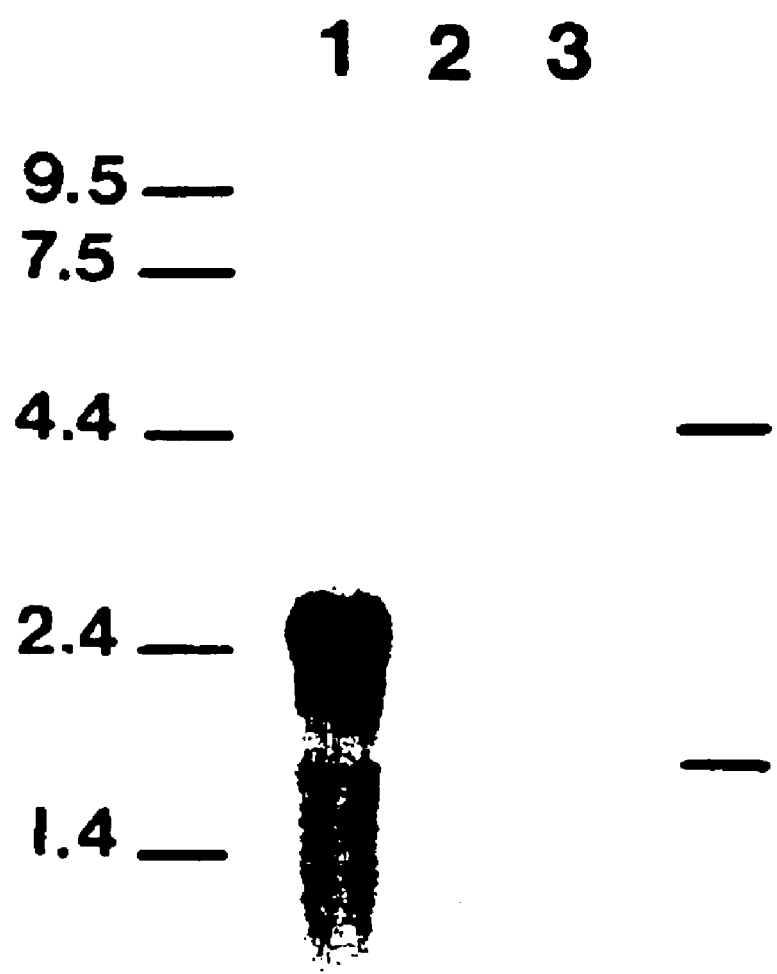
FIG. 11 Autoradiogram of Northern analysis revealing expression of 2.8 kb PSM message unique to the LNCaP cell line (lane 1), and absent from the DU-145 (lane 2) and PC-3 cell lines (lane 3). RNA size ladder is shown on the left (kb), and 28S and 18S ribosomal RNA bands are indicated on the right.
Figure 13:
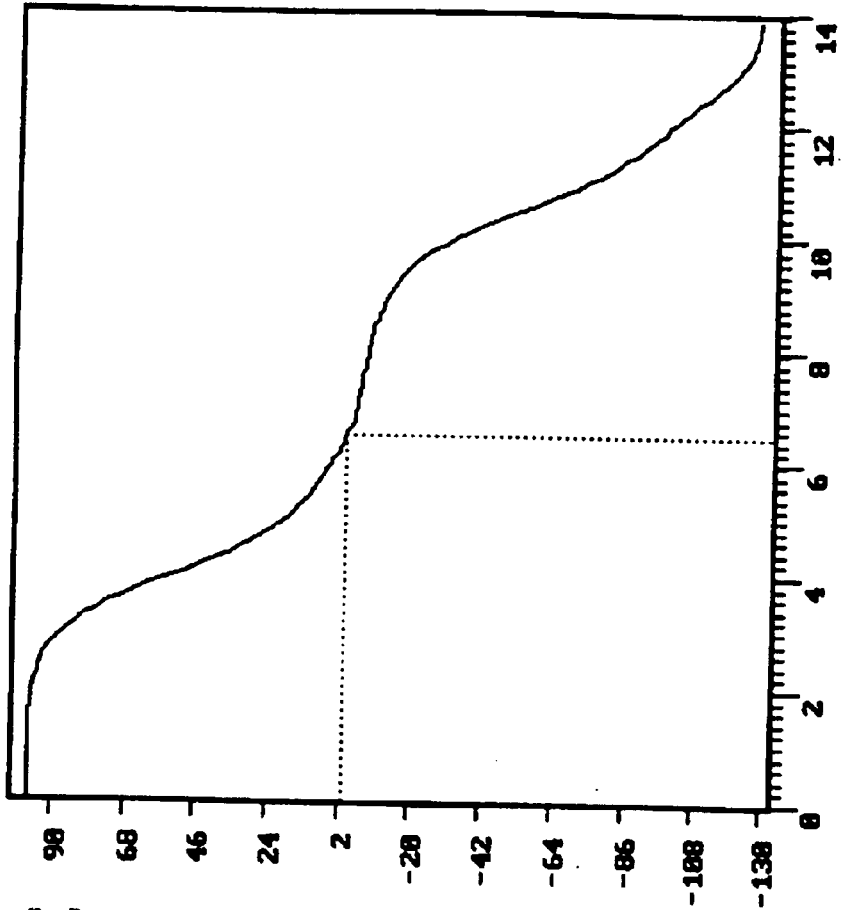

A cDNA library from LNCaP mRNA was constructed using the Superscript® plasmid system (BRL®-Gibco). The library was transformed using competent DH5-α cells and plated onto 100 mm plates containing LB plus 100 µg/ml of Carbenicillin. Plates were grown overnight at 37° C. and colonies were transferred to nitrocellulose filters. Filters were processed and screened as per Grunstein and Hogness (26), using our 1.1 kb partial cDNA homologous probe which was radiolabelled with $^{32}$P-dCTP by random priming (27). We obtained eight positive colonies which upon DNA restriction and sequencing analysis proved to represent full-length cDNA molecules coding for the PSM antigen. Shown in FIG. 7 is an autoradiogram showing the size of the cDNA molecules represented in our library arid in FIG. 8 restriction analysis of several full-length clones is shown. FIG. 9 is a plasmid Southern analysis of the samples in FIG. 8, showing that they all hybridize to the 1.1 kb partial cDNA probe.

Both the cDNA as well as the antigen have been screened through the Genbank Computer database (Human Genome Project) and have been found to be unique.

VIII. Northern Analysis of PSM Gene Expression

Northern analysis (28) of the PSM gene has revealed that expression is limited to the prostate and to prostate carcinoma.

RHA samples (either 10 µg of total RNA or 2 µg of poly A+ RHA) were denatured and electrophoresed through 1.1% agarose/formaldehyde gels at 60 milliamps for 6–8 hours. RHA was then transferred to Nytran® nylon membranes (Schleicher and Schuell®) by pressure blotting in 10×SSC with a Posi-blotter (Stratagene®). RNA was cross-linked to the membranes using a Stratalinker (Stratagene®) and subsequently baked in a vacuum oven at 80° C. for 2 hours. Blots were pre-hybridized at 65° C. for 2 hours in prehybridization solution (BRL®) and subsequently hybridized for 16 hours in hybridization buffer (BRL®) containing 1–2×10$^6$ cpM/ml of $^{32}$P-labelled random-primed cDNA probe. Membranes were washed twice in 1×SSPE/1% SDS and twice in 0.1×SSPE/1% SDS at 42° C. Membranes were then air-dried and autoradiographed for 12–36 hours at −70° C.

IX. PCR Analysis of PSM Gene Expression in Human Prostate Tissues

PCR was performed on 15 human prostate samples to determine PSM gene expression. Five samples each from normal prostate tissue, benign prostatic hyperplasia, and prostate cancer were used (histology confirmed by MSKCC Pathology Department).

10µg of total RNA from each sample was reverse transcribed to made cDNA template as previously described in section IV. The primers used corresponded to the 5' and 3'0 ends of our 1.1 kb partial cDNA, IN-20, and therefore the expected size of the amplified band is 1.1 kb. Since the $T_m$ of our primers is 64° C. we annealed the primers in our PCR at 60° C. We carried out the PCR for 35 cycles using the same conditions previously described in section IV.

LNCaP and H26—Ras transfected LNCaP (29) were included as a positive control and DU-145 as a negative control. 14/15 samples clearly amplified the 1.1 kb band and therefore express the gene.

EXPERIMENTAL RESULTS

Figure 15A:
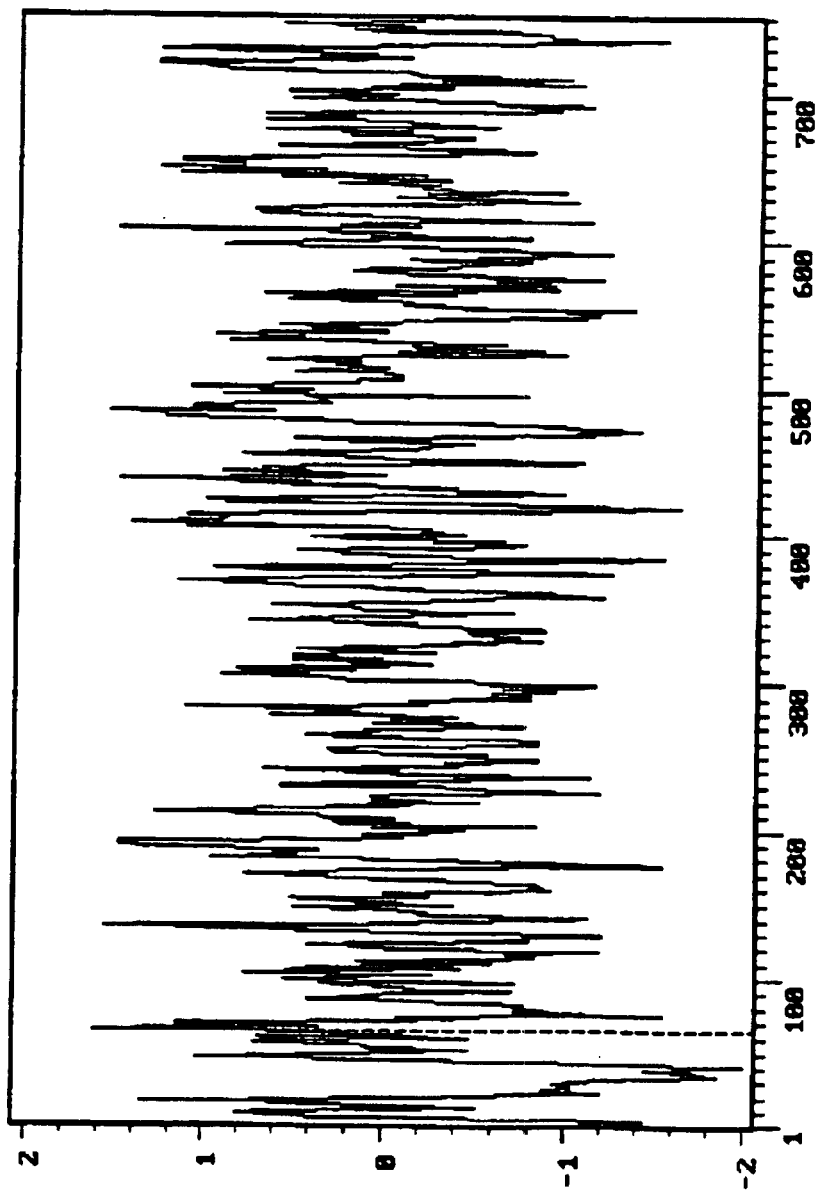
FIG. 15: A Hydrophilicity plot of PSM antigen B. Prediction of membrane spanning segments (SEQ ID NOS: 35–37).

The gene which encodes the 100 kD PSM antigen has been identified. The complete cDNA sequence is shown in Sequence ID #1. Underneath that nucleic acid sequence is the predicted translated amino acid sequence. The total number of the amino acids is 750, ID #2. The hydrophilicity of the predicted protein sequence is shown in FIG. 15A. Shown in FIG. 15B are three peptides with the highest point of hydrophilicity. They are: Asp-Glu-Leu-Lys-Ala-Glu (SEQ ID No. 35); Asn-Glu-Asp-Gly-Asn-Glu (SEQ ID No. 36; and Lys-Ser-Pro-Asp-Glu-Gly (SEQ ID No. 37).

By the method of Klein, Kanehisa and DeLisi, a specific membrane-spanning domain is identified. The sequence is from the amino acid #19 to amino acid #44: Ala-Gly-Ala-Leu-Val-Leu-Aal-Gly-Gly-Phe-Phe-Leu-Leu-Gly-Phe-Leu-Phe (SEQ ID No. 38).

This predicted membrane-spanning domain was computed on PC Gene (computer software program). This data enables prediction of inner and outer membrane domains of the PSM antigen which aids in designing antibodies for uses in targeting and imaging prostate cancer.

When the PSM antigen sequence with other known sequences of the GeneBank were compared, homology between the PSM antigen sequence and the transferrin receptor sequence were found. The data are shown in FIG. 16.

Experimental Discussions
Potential Uses for PSM Antigen:
1. Tumor Detection:
   Microscopic:

Unambiguous tumor designation can be accomplished by use of probes for different antigens. For prostatic cancer, the PSM antigen probe may prove beneficial. Thus PSM could be used for diagnostic purposes and this could be accomplished at the microscopic level using in-situ hybridization using sense (control) and antisense probes derived from the coding region of the cDNA cloned by the applicants. This could be used in assessment of local extraprostatic extension, involvement of lymph node, bone or other metastatic sites. As bone metastasis presents a major problem in prostatic cancer, early detection of metastatic spread is required especially for staging. In some tumors detection of tumor cells in bone marrow portends a grim prognosis and suggests that interventions aimed at metastasis be tried. Detection of PSM antigen expression in bone marrow aspirates or sections may provide such early information. PCR amplification or in-situ hybridization may be used. This could be developed for any possible metastatic region.

2. Antigenic Site Identification

The knowledge of the cDNA for the antigen also provides for the identification of areas that would serve as good antigens for the development of antibodies for use against specific amino acid sequences of the antigen. Such sequences may be at different regions such as outside, membrane or inside of the PSM antigen. The development of these specific antibodies would provide for immunohistochemical identification of the antigen. These derived antibodies could then be developed for use, especially ones that work in paraffin fixed sections as well as frozen section as they have the greatest utility for immunodiagnosis.

3. Restriction Fragment Length Polymorphism and Genomic DNA

Restriction fragment length polymorphisms (RFLPS) have proven to be useful in documenting the progression of genetic damage that occurs during tumor initiation and promotion. It may be that RFLP analysis will demonstrate that changes in PSM sequence restriction mapping may provide evidence of predisposition to risk or malignant potential or progression of the prostatic tumor.

D pending on the chromosomal location of the PSM antigen, the PSM antigen gene may serve as a useful chromosome location marker for chromosome analysis.

4. Serum

With the development of antigen specific antibodies, if the antigen or selected antigen fragments appear in toe serum they may provide for a serum marker for the presence of metastatic disease and be useful individually or in combination with other prostate specific markers.

5. Imaging

As the cDNA sequence implies that the antigen has the characteristics of a membrane spanning protein with the majority of the protein on the exofacial surface, antibodies, especially monoclonal antibodies to the peptide fragments exposed and specific to the tumor may provide for tumor imaging local extension of metastatic tumor or residual tumor following prostatectomy or irradiation. The knowledge of the coding region permits the generation of monoclonal antibodies and these can be used in combination to provide for maximal imaging purposes. Because the antigen shares a similarity with the transferrin receptor based on cDNA analysis (approximately 54%), it may be that there is a specific normal ligand for this antigen and that identification of the ligand(s) would provide another means of imaging.

6. Isolation of Ligands

The PSM antigen can be used to isolate the normal ligand(s) that bind to it. These ligand(s) depending on specificity may be used for targeting, or their serum levels may be predictive of disease status. If it is found that the normal ligand for PSM is a carrier molecule then it may be that PSM could be used to bind to that ligand for therapy purposes (like an iron chelating substance) to help remove the ligand from the circulation. If th ligand promotes tumor growth or metastasis then providing soluble PSM antigen would remove the ligand from binding the prostate. Knowledge of PSM antigen structure could lend to generation of small fragment that binds ligand which could serve the same purpose.

7. Therapeutic Uses a) Ligands. The knowledge that the cDNA structure of PSM antigen shares structural homology with the transferrin receptor (54% on the nucleic acid level) implies that there may be an endogenous ligand for the receptor that may or may not be transferrin-like. Transferrin is thought to be a ligand that transports iron into the cell after binding to the transferrin receptor. However, apotransferrin is being reported to be a growth factor for some cells which express the transferrin receptor (30). Whether transferrin is a ligand for this antigen or some other ligand binds to this ligand remains to be determined. If a ligand is identified it may carry a specific substance such as a metal ion (iron or zinc or other) into the tumor and thus serve as a means to deliver toxic substances (radioactive or cytotoxic chemical i.e. toxin like ricin or cytotoxic alkylating agent or cytotoxic prodrug) to the tumor.

The main metastatic site for prostatic tumor is the bone. The bone and bone stroma are rich in transferrin. Recent studies suggest that this microenvironment is what provides the right "soil" for prostatic metastasis in the bone (31). It may be that this also promotes attachment as well, these factors which reduce this ability may diminish prostatic metastasis to the bone and prostatic metastatic growth in the bone.

It was found that the ligand for the neu antigen (thought to be an oncogen and marker of malignant phenotype in breast carcinoma) served to induce differentiation of breast cancer cells and thus could serve as a treatment for rather than promotor of the disease. It may be that ligand binding to the right region of PSM whether with natural ligand or with an antibody may serve a similar function.

Antibodies against PSM antigen coupled with a cytotoxic agent will be useful to eliminate prostate cancer cells. Transferrin receptor antibodies with toxin conjugates are cytotoxic to a number of tumor cells as tumor cells tend to express increased levels of transferrin receptor (32). Transferrin receptors take up molecules into the cell by endocytosis. Antibody drug combinations can be toxic. Transferrin linked toxin can be toxic.

b) Antibodies against PSM antigen coupled with a cytotoxic agent will be useful to eliminate prostate cancer cells. The cytotoxic agent may be a radioisotope or toxin as known in ordinary skill of the art. The linkage of the antibody and the toxin or radioisotope can be chemical. Examples of direct linked toxins are doxorubicin, chlorambucil, ricin, pseudomonas exotoxin etc., or a hybrid toxin can be generated ½ with specificity for PSM and the other ½ with specificity for the toxin. Such a bivalent molecule can serve to bind to the tumor and the other ½ to deliver a cytotoxic to the tumor or to bind to and activate a cytotoxic lymphocyte such as binding to the $T_1$–$T_3$ receptor complex. Antibodies of required specificity can also be cloned into T cells and by replacing the immunoglobulin domain of the T cell receptor (TcR); cloning in the desired MAb heavy and light chains; splicing the $U_h$ and $U_L$ gene segments with the constant regions of the α and 62 TCR chains and transfecting these chimeric Ab/TcR genes in the patients' T cells, propagating these hybrid cells and infusing them into the patient (33). Specific knowledge of tissue specific antigens for targets and generation of MAb's specific for such targets will help make this a usable approach. Because the PSM antigen coding region provides knowledge of the entire coding region, it is possible to generate a number of antibodies which could then be used in combination to achieve an additive or synergistic anti-tumor action. The antibodies can be linked to enzymes which can activate non-toxic prodrugs at its site of the tumor such as Ab-carboxypeptidase and 4-(bis(2 chloroethyl)amino) benzoyl-α-glutamic acid and its active parent drug in mice (34).

It is possible to produce a toxic genetic chimera such as TP-40 a genetic recombinant that possesses the cDNA from TGF-alpha and the toxic portion of pseudomonas exotoxin so the TGF and portion of the hybrid binds the epidermal growth factor receptor (EGFR) and the pseudomonas portion gets taken up into the cell enzymatically and inactivates the ribosomes ability to perform protein synthesis resulting in cell death. When we know the ligand for the PSM antigen we can do the same.

In addition, once the ligand for the PSM antigen is identified, toxin can be chemically conjugated to the ligands. Such conjugated ligands can be therapeutically useful. Examples of the toxins are daunomycin, chlorambucil, ricin, pseudomonas exotoxin, etc. Alternatively, chimeric construct can be created linking the cDNA of the ligand with the cDNA of the toxin. An example of such toxin is TGFα and pseudomonas exotoxin (35).

8. Others

The PSM antigen may have other uses. It is well known that the prostate is rich in zinc, if the antigen provides function relative to this or other biologic function the PSM antigen may provide for utility in the treatment of other prostatic pathologies such as benign hyperplastic growth and/or prostatitis.

Because purified PSM antigen can be generated, the purified PSM antigen can be linked to beads and use it like a standard "affinity" purification. Serum, urine or other biological samples can be used to incubate with the PSM antigen bound onto beads. The beads may be washed thoroughly and then eluted with salt or pH gradient. The eluted material is SDS gel purified and used as a sample for microsequencing. The sequences will be compared with other known proteins and if unique, the technique of degenerated PCR can be employed for obtaining the ligand. Once known, the affinity of the ligand will be determined by standard protocols (15).

REFERENCES

1. Chiaroda, A. (1991) National roundtable of prostate cancer: research directions. Cancer Res. 51: 2498–2505.
2. Warner, J. A., et al., (1991) Future developments of non-hormonal systemic therapy for prostatic carcinoma. Urologic Clin. North Amer. 18:25–33.
3. Nguyen, L., et al., (1990) Prostatic acid phosphatase in the serum of cancer patients with prostatic cancer is a specific phosphotyrosine acid phosphatase. Clin. Chem. 35:1450–1455.
4. Henttu, P., et al., (1989) cDNA coding for the entire human prostate specific antigen show high homologies to the human tissue kallikrein genes. Bioch. Biophys. Res. Comm. 160:903–908.
5. Yong, CY-F., et al., (1991) Hormonal regulation of prostate-specific antigen messenger RNA in human prostatic adenocarcinoma cell line LNCaP. Cancer Res. 51:3748–3752.
6. Liotta, L. A. (1986) Tumor invasion and metastases: role of the extracellular matrix. Cancer Res. 46:1–7.
7. Horoszewicz, J. S., et al. (1987) Monoclonal antibodies to a new antigenic marker in epithelial prostatic cells and serum of prostatic cancer patients. Anticancer Res. 7:927–936.
8. Horoszewicz, J. S., et al. (1983) LNCaP model of human prostatic carcinoma. Cancer Res., 43:1809–1818.
9. Lopes, D., et al. (1990) Immunohistochemical and pharmacokinetic characterization of the site-specific immunoconjugate CYT-356, derived from anti-prostate monoclonal antibody 7E11-C5. Cancer Res., 50:6423–6429.

10. Wright, Jr., et al., (1990) Characterization of a new carcinoma associated marker:7E11-C5. Antibod. Immunoconj. Radiopharm.3:(abst#193).
11. Feng, Q., et al., (1991) Purification and biochemical characterization of the 7E11-C5 prostate carcinoma associated antigen. Proc. Amer. Assoc. Cancer Res. 32:239.
12. Axelrod, H. R., et al., Preclinical results and human immunohistochemical studies with $^{90}$Y-CYT-356. A New prostate cancer agent. Abstract 596. AUA 87th Annual Meeting, May 10–14, 1992. Washington, D.C.
13. Maniatis, T., et al., (1982) Molecular Cloning; Cold Spring Harbor Laboratory, pp.197–98 (1982).
14. Maniatis, et al., (1982) Molecular Cloning, Cold Spring Harbor Laboratory.
15. Methods in Enzymology vol. 34: 1–810, 1974 (E) B. Jacoby and M. Wilchek Academic Press, New York 1974.
16. Hogan B. et al. (1986) Manipulating the Mouse Embryo, A Laboratory Manual, Cold Spring Harbor Laboratory.
17. Capecchi M. R. Science (1989) 244:1288–1292; Zimmer, A. and Gruss, P. (1989) Nature 338:150–153.
18. Trowbridge, I. S., (1982) Prospects for the clinical us e of cytotoxic monoclonal antibodies conjugates in the treatment of cancer. Cancer Surveys 1:543–556.
19. Hank, S. K. (1987) Homology probing: identification of cDNA clones encoding members of the protein-serine kinase family. Proc. Natl. Acad. Sci. 84:388–392.
20. Lee, C. C., et al., (1988) Generation of cDNA probes directed by amino acid sequences: cloning of urate oxidase. Science, 239, 18288
21. Girgis, S. I., et al. (1988) Generation of DNA probes for peptides with highly degenerate codons using mixed primer PCR. Nucleic Acids Res. 16:10932.
22. Kartner, N., et al. (1977) Isolation of plasma membranes from human skin fibroblasts. J. Membrane Biology, 36:191–211.
23. Hsu, S. M., et al. (1981) Comparative study of the immunoperoxidasie, anti-peroxidase, and avidin-biotin complex method for studying polypeptide hormones with radioimmunoassay antibodies. Am. J. Pathology, 75:734.
24. Tempst, P., et al. (1989) Examination of automated polypeptide sequencing using standard phenylisothiocyanate reagent and subpicozaole high performance liquid chromatography analysis. Analytical Biochem. 183:290–300.
25. Birnboim, H. C. (1983) A rapid alkaline extraction method for the isolation of plasmid DNA. Meth. Enzymol, 100:243–255.
26. Sanger, F., et al. (1977) DNA sequencing with chain-terminating inhibitors. Proc. Natl. Acad. Sci. USA, 74:5463–5467.
27. Grunstein, M., et al. (1975) colony hybridization as a method for the isolation of cloned DNAs that contain a specific gene. Proc. Natl. Acad. Sci. USA, 72:3961.
28. Feinberg, A. P., et al. (1983) A technique for radiolabeling DNA restriction endonuclease fragments to high specific activity. Anal. Biochem, 132, 6.
29. Rave, N., et al. (1979) Identification of procollagen mRNAs transferred to diazobenzylomethyl paper from formaldehyde gels. Nucleic Acids Research, 6:3559.
30. Voeller, H. J., et al. (1991) v-ras$^H$ expression confers hormone-independent in-vitro growth to LNCaP prostate carcinoma cells. Molec. Endocrinology. Vol. 5. No. 2, 209–216.
31. Sirbasku, D. A. (1991) Purification of an equine apotransferrin variant (thyromedin) essential for thyroid hormone dependent growth of $GH_1$, rat pituitary tumor cells in chemically defined culture. Biochem., 30:295–301.
32. Rossi, M. C. (1992) Selective stimulation of prostatic carcinoma cell proliferation by transferrin. Proc. Natl. Acad. Sci. (USA) 89:6197–6201.
33. Eshhan, Z. (1990) Chimeric T cell receptor which incorporates the anti-tumor specificity of a monoclonal antibody with the cytolytic activity of T cells: a model system for immunotherapeutic approach. B. J. Cancer 62:27–29.
34. Antoniw, P. (1990) Disposition of the prodrug 4-(bis(2 chloroethyl) amino)benzoyl-α-glutamic acid and its active parent in mice. B. J. Cancer 62:905–914.
35. Heimbrook, D. C., et al. (1990) Transforming growth factor alpha-pseudomonas exotoxin fusion protein prolongs survival of nude mice bearing tumor xenografts. Proc. Natl. Acad. Sci. (USA) 87:4697–4701.

What is claimed is:

1. A purified prostate specific membrane antigen polypeptide comprising an antigenic fragment of human prostate specific membrane antigen, which fragment has within its structure consecutive amino acids having the sequence Asp-Glu-Leu-Lys-Ala-Glu (SEQ ID NO: 35) and additional consecutive amino acids, provided that the sequence of the polypeptide is included within SEQ ID NO:2.

2. A purified prostate specific membrane antigen polypeptide comprising an antigenic fragment of human prostate specific membrane antigen, which fragment has within its structure consecutive amino acids having the sequence Asn-Glu-Asp-Gly-Asn-Glu (SEQ ID NO: 36) and additional consecutive amino acids, provided that the sequence of the polypeptide is included within SEQ ID NO:2.

3. A purified prostate specific membrane antigen polypeptide comprising an antigenic fragment of human prostate specific membrane antigen, which fragment has within its structure consecutive amino acids having the sequence Lya-Ser-Pro-Asp-Glu-Gly (SEQ ID NO: 37).

4. A purified prostate specific membrane antigen polypeptide comprising an antigenic fragment of human prostate specific membrane antigen, which fragment has within its structure consecutive amino acids having the sequence Ala-Gly-Ala-Leu-Val-Leu-Ala-Gly-Gly-Phe-Phe-Leu-Leu-Gly-Phe-Leu-Phe (SEQ ID NO: 38).

5. A purified prostate specific membrane antigen polypeptide comprising an antigenic fragment of human prostate specific membrane antigen, which fragment has within its structure consecutive amino acids having the following sequences:
   (a) Asp-Glu-Leu-Lys-Ala-Glu (SEQ ID NO: 35);
   (b) Asn-Glu-Asp-Gly-Asn-Glu (SEQ ID NO: 36); and
   (c) Lys-Ser-Pro-Asp-Glu-Gly (SEQ ID NO: 37).

6. A purified prostate specific membrane antigen polypeptide comprising an antigenic fragment of human prostate specific membrane antigen, which fragment has within its structure consecutive amino acids having the following sequences:
   (a) Asp-Glu-Leu-Lys-Ala-Glu (SEQ ID NO: 35);
   (b) Asn-Glu-Asp-Gly-Asn-Glu (SEQ ID NO: 36);
   (c) Lys-Ser-Pro-Asp-Glu-Gly (SEQ ID NO: 37); and
   (d) Ala-Gly-Ala-Leu-Val-Leu-Ala-Gly-Gly-Phe-Phe-Leu-Leu-Gly-Phe-Leu-Phe (SEQ ID NO: 38).

7. A purified antigenic prostate specific membrane antigen polypeptide having within its structure consecutive amino acids having the sequence set forth in SEQ ID NO: 2.

8. A purified antigenic prostate specific membrane antigen polypeptide consisting of consecutive amino acids, the sequence of which is within the sequence of the outside region of human prostate specific membrane antigen, the sequence of which antigen is set forth in SEQ ID NO:2, provided that if the polypeptide comprises consecutive amino acids having the sequence set forth in SEQ ID NO:35 or 36, the polypeptide further comprises additional amino acids.

9. A purified prostate specific membrane antigen polypeptide comprising an antigenic fragment of human prostate specific membrane antigen, which fragment has a sequence which is the same as a sequence within the outside region of prostate specific membrane antigen, the sequence of which antigen is set forth in SEQ ID NO:2, and the sequence of which polypeptide comprises, within its structure, consecutive amino acids having a sequence selected from the group consisting of:
   (a) Asn-Glu-Asp-Gly-Asn-Glu (SEQ ID NO:36);
   (b) Lys-Ser-Pro-Asp-Glu-Gly (SEQ ID NO:37); and
   (c) Ala-Gly-Ala-Leu-Val-Leu-Ala-Gly-Gly-Phe-Phe-Leu-Leu-Gly-Phe-Leu-Phe (SEQ ID NO: 38)
provided that if the antigenic fragment comprises consecutive amino acids having the sequence set forth in SEQ ID NO:35 or 36, the antigenic fragment further comprises additional amino acids.

10. A purified prostate specific membrane antigen polypeptide comprising an antigenic fragment of human prostate specific membrane antigen, which fragment has a sequence which is the same as a sequence within the outside region of prostate specific membrane antigen, the sequence of which antigen is set forth in SEQ ID NO:2, wherein the antigenic fragment generates as an immunogen antibodies specific to PSM antigen, and said antigenic fragment comprises consecutive amino acids having a sequence selected from the group consisting of SEQ ID NO:35 or 36, SEQ ID NO:36, SEQ ID NO:37, or SEQ ID NO:38, provided that if the antigenic fragment comprises consecutive amino acids having the sequence set forth in SEQ ID NO:35, the antigenic fragment further comprises at least one additional amino acid present in SEQ ID NO:2, provided that the sequence of the antigenic fragment is included within SEQ ID NO:2.

* * * * *